United States Patent [19]

Khan et al.

[11] Patent Number: 5,798,032

[45] Date of Patent: Aug. 25, 1998

[54] METHOD AND APPARATUS FOR AUTOMATED CARBOHYDRATE MAPPING AND SEQUENCING

[75] Inventors: Shaheer H. Khan, Foster City; Roger A. O'Neill, San Carlos; Louis B. Hoff, Belmont, all of Calif.

[73] Assignee: The Perkin-Elmer Corporation, Foster City, Calif.

[21] Appl. No.: 558,047

[22] Filed: Nov. 13, 1995

Related U.S. Application Data

[63] Continuation of Ser. No. 307,206, Sep. 16, 1994, abandoned, which is a continuation-in-part of Ser. No. 252,657, Jun. 2, 1994, abandoned.

[51] Int. Cl.$^6$ .................. C25B 7/00; C25B 9/00
[52] U.S. Cl. .......... 204/452; 204/451; 204/450; 204/600; 204/601; 204/603
[58] Field of Search .................. 204/451, 450, 204/452, 600, 601, 603; 536/127

[56] References Cited

U.S. PATENT DOCUMENTS

| | | | |
|---|---|---|---|
| 4,936,974 | 6/1990 | Rose et al. | 204/299 R |
| 4,975,165 | 2/1990 | Brandley | 204/461 |
| 5,019,231 | 2/1990 | Brandley et al. | 204/461 |
| 5,110,431 | 2/1990 | Moring | 204/451 |
| 5,132,432 | 9/1989 | Haughland et al. | 548/518 |
| 5,180,479 | 1/1993 | Rose, Jr. | 204/299 R |
| 5,240,577 | 8/1993 | Jorgenson et al. | 204/180.1 |
| 5,292,416 | 3/1994 | Novotny et al. | 204/182.8 |
| 5,310,462 | 5/1994 | Chen | 204/180.1 |
| 5,310,463 | 5/1994 | Dadoo et al. | 204/180.1 |
| 5,358,612 | 10/1994 | Dasgupta et al. | 204/180.1 |
| 5,378,334 | 1/1995 | Dadoo et al. | 204/180.1 |

OTHER PUBLICATIONS

Lemmo et al. Analytical Chemistry, 65, (11): 1576–1581 (1993) Transverse Flow Gating for the Coupling of Microcolumn LC with CZE in a Comprehensive Two–Dimensional System.

Chisea et al., "Capillary Zone Electrophoresis of Malto–Oligo . . . ", *J. Chromatography* 645:337–352 (1993).

Whitaker et al., Cascade Blue Derivatives . . . *J. Anal. Biochemistry*, 198: 119–130 (1991).

Jackson, et al. Anal. Biochem., 216: 243–252 (1994) The Analysis of Fluorophore–Labeled Glycans by High–Resolution Polyacrylamide Gel Electrophoresis.

Yamashita et al. Methods in Enzymology vol. 83, Ginsburg, ed., Academic Press, San Diego, CA (1982) Analysis of Oligsaccharides by Gel Filtration.

Honda et al. Anal. Biochem., 176: 72–77 (1989) Simultaneous Determination of Reducing Monosaccharides by Capillary Electrophoresis as the Borate Complexes of N–2–Pyridylglycamines.

(List continued on next page.)

*Primary Examiner*—Cecilia J. Tsang
*Assistant Examiner*—C. Delacroix-Muirheid
*Attorney, Agent, or Firm*—Paul D. Grossman

[57] ABSTRACT

Methods and apparatus are disclosed for improved mapping and sequencing of carbohydrate polymers. In one aspect, the improvement includes a means for coupling two capillary electrophoresis (CE) tubes in such a way so as to (i) efficiently transfer a selected sample component from a first CE capillary to a second CE capillary or, (ii) introduce a supplementary reagent into the separation path between the two capillaries, e.g., an internal standard, binding agent, enzyme, and the like. In an additional aspect, the invention includes improved apparatus and methods for electrophoresis of labeled carbohydrates in which a sample carbohydrate labeled with a first label is separated by CE and its migration behavior is compared with an internal standard labeled with one or more second labels which are distinguishable from the first label. In yet another aspect, the invention includes improved method and apparatus for sequencing carbohydrates in which a sample mixture is separated in a first CE dimension, a component of the sample mixture is selected, the selected component is incubated with an enzyme reagent, the reaction products are separated in a second CE dimension, the electrophoretic behavior of the reaction products is correlated with the known specificity of the enzyme reagent, and the process is repeated to determine the complete sequence of the carbohydrate sample.

13 Claims, 17 Drawing Sheets

OTHER PUBLICATIONS

Chiesa et al. J. Chromatogr. 645: 337–352 (1993) Capillary Zone Electrophoresis of Malto–Oligosaccharides Derivatized with 8–Aminonaphthalene–1, 3, 6–Trisulfonic Acid.

Suzuki, et al. Anal. Biochem., 205: 227–236 (1992) Two–Dimensional mapping of N–Glycosidically Linked Asialo–Oligosaccharides from glycoproteins as Reductively Pyridylaminated Derivatives using Duel Separation Modes of High–Performance Capillary Electrophoresis.

Edge et al. Proc. Natl. Acad. Sci. USA, 89: 6338–6342 (1992) Fast Sequencing of Oligosaccharides: The Reagent–Array Analysis Method.

Prakash et al. Anal. Biochem., 128: 41–46 (1983) A New Fluorescent Tag for Labeling Saccharides.

Liu, et al. Anal. Chem., 63: 408–412 (1991) Design of 3-(4-carboxybenzoyl)-2-quinolinecarboxaldehyde as a Reagent for Ultrasensitive Determination of Primary Amines by Capillary Electroforesis using laser Fluorescence Detection.

Honda et al. J .Chromatgr., 608:289–295 (1992) High Performance Capillary Electrophoresis of Unsaturated Oligosaccharides Derived From Glycoaminoglycans by Digestion with Chondroitinase ABC as 1–phenyl–3–methyl–5–pyrazolone Derivatives.

Liu et al. Proc. Natl. Acad. Sci. 88: 2302–2306 (1991) Ultrasensitive Fluorometric Detection of Carbohydrates as Derivatives in Mixtures Separated by Capillary Electrophoresis.

Zhao, et al. Glycobiology, 4: 239–242 (1994) Detection of 100 Molecules of Product Formed in a Fucosyltransferase Reaction.

Tomiya et al. Anal. Biochem., 171: 73–90 (1988) Analysis of N–Linked Oligosaccharides using a Two–Dimensional Mapping Technique.

Whitaker et al. Anal. Biochem., 198: 119–130 (1991) Cascade Blue Derivatives: Water Soluble, Reactive, Blue Emission Dyes Evaluated as Fluorescent Labels and Tracers.

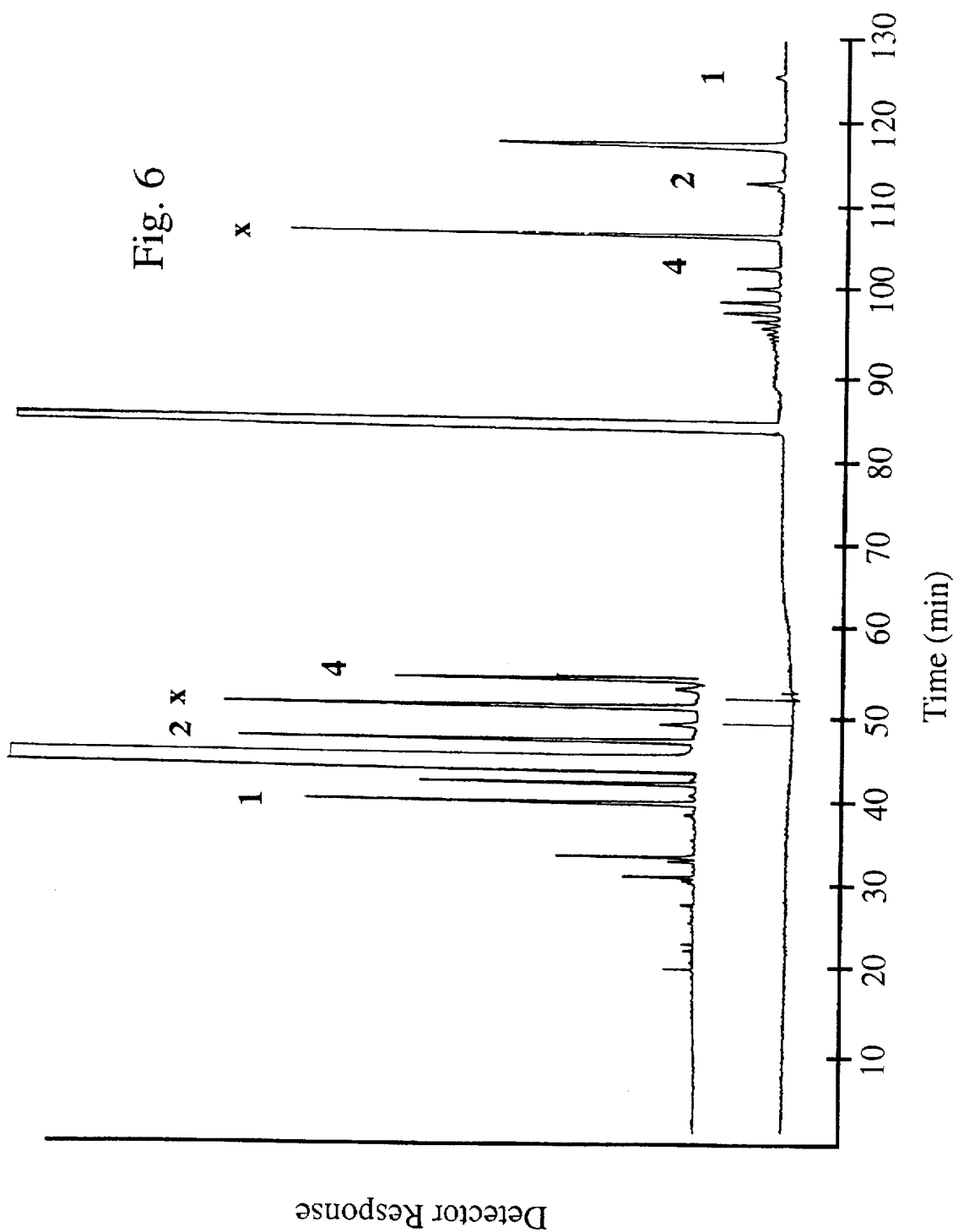

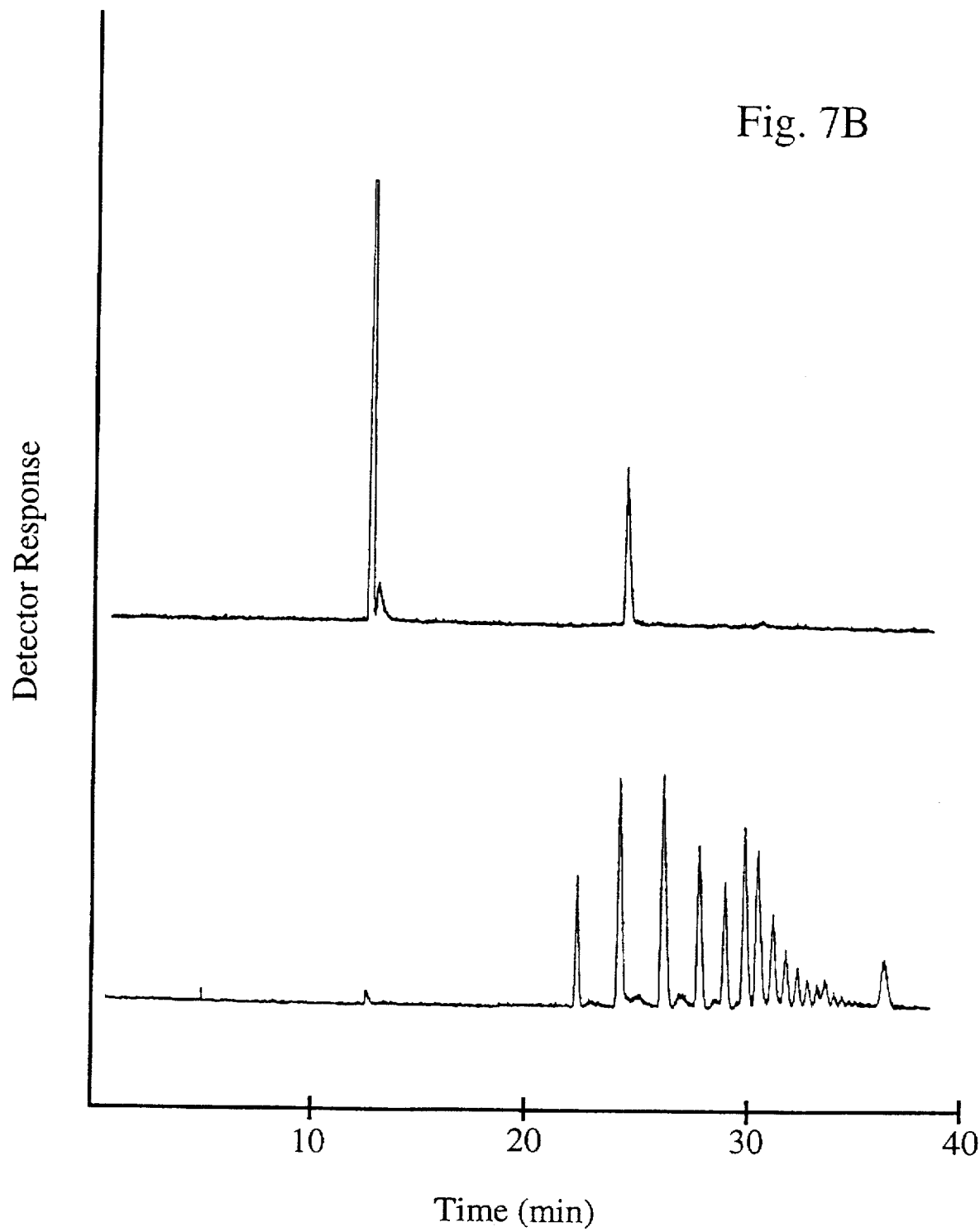

METHOD AND APPARATUS FOR AUTOMATED CARBOHYDRATE MAPPING AND SEQUENCING

This is a continuation of application Ser. No. 08/307,206 filed Sep. 16, 1994 now abandoned, which is a continuation-in-part of Ser. No. 08/252,657, filed Jun. 02, 1994 now abandoned

BACKGROUND OF THE INVENTION

The present invention relates to carbohydrate analysis, and in particular to automated systems and methods for the characterization of carbohydrate structure.

The elucidation of carbohydrate structure in biological systems is an increasingly important problem in modern life science research and applications. The reason for this increased interest in carbohydrate structure is the realization that complex carbohydrates have many important biological roles. For example, when attached to polypeptides, carbohydrates determine the correct folding, provide protection against degradation, increase the solubility and stability, and determine the intracellular and/or intracellular destination of the polypeptide chain. Carbohydrates are also involved in intercellular signaling processes, and act as markers for tumor cells and for cellular differentiation. Recently, a number of glycoproteins have been applied clinically as biopharmaceuticals, e.g., recombinant erythropoietin, glucocerebrosidase, and recombinant tissue plasminogen activator, wherein variations in the potency, pharmacokinetics and antigenicity of these molecules may be attributable to their carbohydrate structure. The determination of the structures of oligosacccharides has therefore become essential not only for understanding fundamental biological process, but also for commercial and therapeutic reasons.

The challenge facing the carbohydrate analyst is formidable. Unlike proteins and DNA, where molecular structure is determined by the linear sequence of amino acids or nucleotide bases, respectively, carbohydrates have additional variable features. The fundamental data required to fully characterize a carbohydrate structure are the monosaccharide composition, the order, number, configuration, and ring form of the saccharide residues, the position and character of any substituient groups on any residue, the positions of the interresidue linkages including any branching points, and the configuration of the glycosidic linkages.

One important class of techniques which is used to characterize carbohydrates is mapping. In mapping techniques, the separation profile of an unknown sample is compared with that of a known, pre-characterized species. By comparing the elution properties of the sample with that of the pre-characterized species, in many cases the structure of the sample can be deduced. While mapping techniques do not provide the kind of detailed unambiguous structural information that is available from more fundamental measurements, such as nuclear magnetic resonance or mass spectrometry, the speed, sensitivity, and simplicity of mapping techniques makes them a powerful analytical option.

An important subclass of carbohydrate mapping techniques is that utilizing an electrophoretic separation. In electrophoretic mapping of carbohydrates, the sample is first derivatized with an agent which renders the carbohydrate charged, so that it will migrate in an electric field, and detectable. The derivatized sample is then subjected to electrophoresis, e.g., Jackson, Anal. Biochem., 216: 243–252 (1994), this reference being herein incorporated by reference. Typically, the migration behavior of the sample is compared with that of a pre-characterized species.

Oligosaccharide sequencing can be performed using mapping techniques in conjunction with pre-separation enzyme treatment. In one preferred sequencing method, after the sample is derivatized but before the electrophoresis, the sample is divided into aliquots and each aliquot is treated with an ordered array of specific carbohydrate-cleaving enzymes whose cleaving properties are well known, e.g. exo- and endoglycosidases. By correlating the migration behavior of the enzymatic cleavage products with the specificity of each enzyme, the complete oligosaccharide sequence can be determined, e.g., Edge, et al., Proc.Natl.Acad.Sci. USA, 89: 6338–6342 (1992), this reference being herein incorporated by reference.

The ultimate quality of a mapping experiment is closely related to the accuracy and precision with which the migration behavior of the sample and standard is measured. One method used to increase the accuracy and precision of electrophoretic measurements is to use an internal standard, i.e., a standard which is run simultaneously with the sample. In order to insure that the signal from the internal standard does not interfere with that from the sample, it is preferable to use a detection means which can distinguish between the internal standard and the sample. An example of this approach in the area of carbohydrate analysis is provided by Yamashita, where the internal standard is monitored by refractive index detection and the radioactively-labeled sample is detected using a radioactivity monitor. See Yamashita et al., Methods in Enzymology Vol. 83, Ginsburg, ed., Academic Press, San Diego, Calif. (1982), this reference being herein incorporated by reference. However, because the technique requires radioactivity, it is cumbersome and dangerous to practice.

Another important aspect of mapping is the selectivity of the separation step. One means used to increase the selectivity of the separation is to perform a two-dimensional (2-D) separation, i.e., to perform two coupled separations, one after the other, wherein the first and second separation "dimensions" utilize different separation conditions. Brandley describes a method for 2-D gel electrophoresis of carbohydrates in which the first dimension uses a borate-containing buffer, and the second dimension uses a glycine-containing buffer, wherein, after the first electrophoresis dimension, the sample band is manually cut from the first-dimension gel and loaded onto the second-dimension gel, e.g., Brandley, U.S. Pat. No. 4,975,165. Tomiya shows a 2-D chromatographic method which utilizes reverse phase and size exclusion dimensions, e.g., Tomiya et al., Anal. Biochem., 171: 73–90 (1988). While this approach achieves the extra resolving power of 2-D electrophoresis, it requires a number of additional manual manipulations.

Another method which is used to increase the selectivity of an electrophoretic mapping experiment is "blotting", wherein, after the sample has been run on an electrophoresis gel, it is transferred onto a membrane where it is probed with specific probing reagents, e.g., antibody, lectin, and the like, e.g., Brandley et al., U.S. Pat. No. 5,019,231, this reference being herein incorporated by reference. As with the above described 2-D separation technique, as presently practiced, post-separation probing provides an added degree of selectivity, but has the drawback of imposing additional time consuming manual steps.

As classically practiced, the above described electrophoretic mapping techniques rely on slab gel electrophoresis, a technique which is slow, labor intensive, and not amenable to automation. Recently, capillary electrophoresis (CE) has been recognized as a powerful alternative to traditional electrophoretic techniques for the analysis of carbohydrates because of several technical advantages: (i) CE capillaries have high surface-area—to-volume ratios leading to efficient dissipation of the Joule heat produced by the electrophoresis which, in turn, permits the use of high electrical fields, resulting in faster analyses and superior resolution; (ii) CE permits the use of alternative separation media by removing the requirement that the separation medium serve as an anti-convective support; (iii) CE requires minimal sample volumes; and, (iv) CE is amenable to automation, particularly of the medium preparation, sample loading and peak detection operations, e.g., Honda et al., Anal. Biochem.: 176, 72–77 (1989), Chiesa et al., J. Chromatogr. 645: 337–352 (1993), Grossman et al., editors, Capillary Electrophoresis (Academic Press, San Diego, 1992). Suzuki has shown the power of using 2-D CE separations by serially performing two CE separations wherein each separation utilizes a different separation buffer, e.g., Suzuki, et al., Anal.Biochem., 205: 227–236 (1992).

The foregoing illustrates limitations to the known prior art. Ideally, an electrophoretic carbohydrate mapping and/or sequencing method should (i) allow for the pre-electrophoresis treatment of the sample with selected carbohydrate-digesting enzymes, (ii) include a differentially-detectable internal standard which does not require radioactivity, (iii) provide a multi-dimensional electrophoretic separation, (iv) have the ability to accommodate a post-separation probing step, and, (iv) allow for convenient automated operation.

SUMMARY OF THE INVENTION

The present invention provides improved methods and apparatus for mapping and sequencing carbohydrate polymers.

In one aspect, the invention includes apparatus and methods for automated multidimensional electrophoresis of sample molecules, wherein the improvement includes a means for coupling two capillary electrophoresis tubes such that a selected component can be transferred from a first CE capillary to a second CE capillary.

In another aspect, the invention includes improved apparatus and methods for multi-dimensional electrophoresis of sample molecules, wherein the improvement includes a means for coupling, two capillary electrophoresis tubes in such a way so as to efficiently transfer a selected sample component from a first CE capillary to a second CE capillary while simultaneously introducing a supplementary reagent into the separation path between the two capillaries, e.g., an internal standard, binding agent, enzyme, and the like, which are particularly useful in carbohydrate mapping and/or sequencing In an additional aspect, the invention includes improved apparatus and methods for electrophoresis of labeled carbohydrates in which a sample carbohydrate labeled with a first label is separated by CE and its migration behavior is compared with one or more internal standards labeled with one or more second labels which are distinguishable from the first label.

In yet another aspect, the invention includes improved apparatus and methods for automated sequencing of carbohydrates in which a sample mixture is separated in a first CE dimension, a component of the sample mixture is selected, the selected component is treated with an enzyme reagent, the reaction products are separated in a second CE dimension, the electrophoretic behavior of the reaction products is correlated with the known specificity of the enzyme reagent, and the process is repeated to determine the sequence of the carbohydrate sample.

BRIEF DESCRIPTION OF THE DRAWINGS

FIG. 6 is an example showing the transfer of a sample peak between two CE capillaries connected by a transfer cell and the simultaneous introduction of an internal standard according to the present invention.

FIGS. 7A–7G are examples showing two-color fluorescence detection of differentially labeled sample (top) and internal standard (bottom).

DETAILED DESCRIPTION OF THE INVENTION

I. DEFINITIONS

Figure 1:
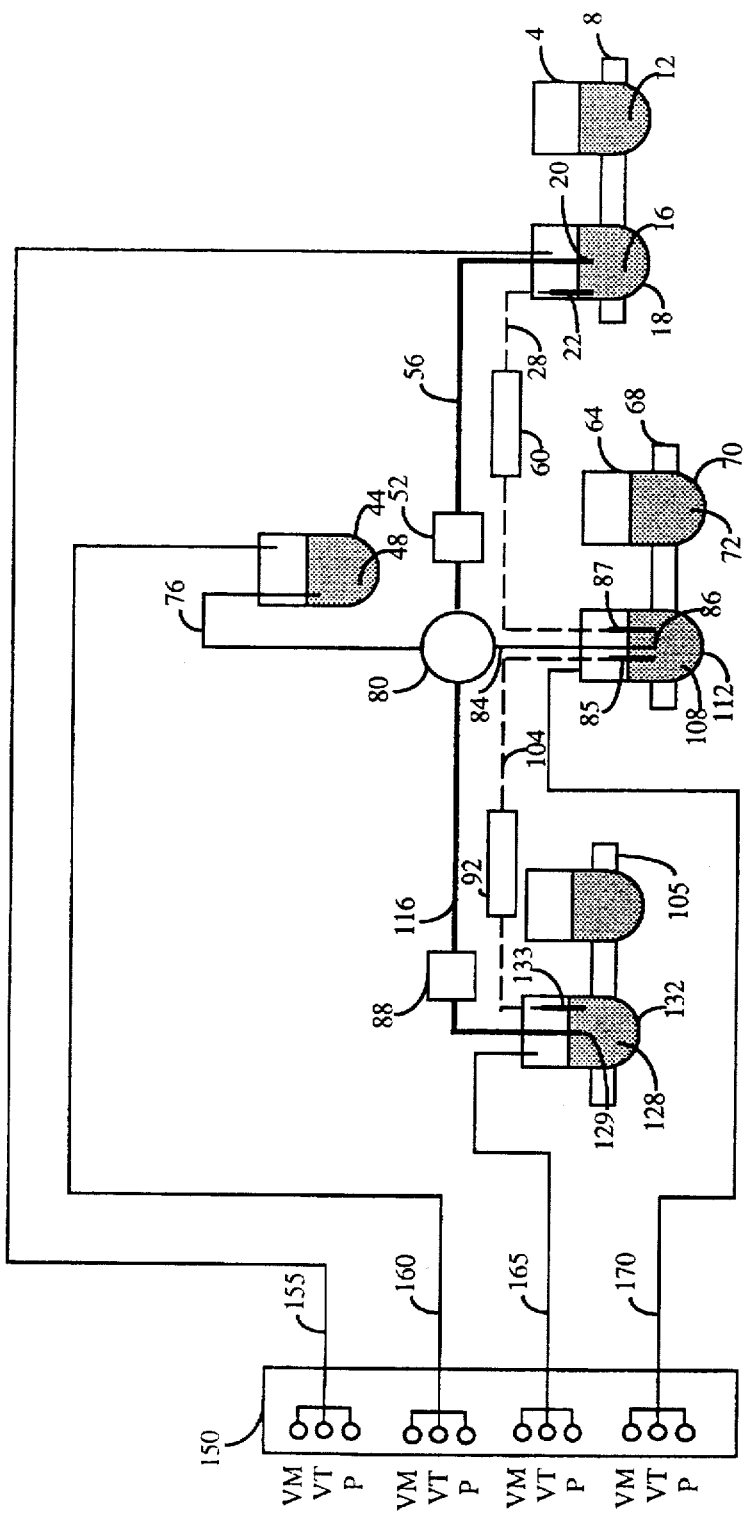
FIG. 1 is a schematic diagram of the carbohydrate analyzer of the present invention.

As used herein, the terms "carbohydrate", "sugar", or "oligosaccharide" refer to the group of chemical species partially represented by the general formula $C_x(H_2O)_y$, where x is six, or an integral multiple of six, and y is any integer greater than or equal to one. In addition, modified versions of the above structures are intended, e.g., sugar sulfates, sugar phosphates, amino sugars, acetylamino sugars, N-sulfo sugars, O-acetylated sugars, deoxy sugars, pyrvate, glycolylamino sugars, uronic acid, methylated sugars, acetylated sugars, and the like.

The term "internal standard" or "standard" as used herein refers to one or a mixture of characterized chemical species which are mixed with the sample prior to electrophoresis in order to improve the characterization of the sample.

As used herein, the term "mapping" refers to the technique whereby a sample is characterized by its electrophoretic or chromatographic migration properties, specifically its electrophoretic mobility, relative electrophoretic mobility with respect to a standard, retention time, relative retention time with respect to a standard, and the like.

As used herein, the term "sequencing" refers to methods used to determine the order, configuration and ring form of the saccharide residues, the positions of interresidue linkages including any branching points, and the configuration of the glycosidic linkages in a carbohydrate polymer.

The term "separation medium" as used herein refers to the medium in which the electrophoretic separation is performed. The separation medium can be a buffer solution, a cross-linked gel network, a polymer solution, a micellar solution, and the like. In the case of a rigid-gel medium, the separation medium may contain two components: a gel component, located within the capillary, and a running-buffer component, located in the buffer reservoir.

As used herein, the term "two-dimensional separation" or "2-D separation or "two-dimensional electrophoresis" refers to a separation which takes place in two steps, wherein a supplementary reagent is added into the separation path between the steps, and/or the separation medium used in each step is different.

The term "label" as used herein refers to a chemical species which enhances the detectability of the sample or internal standard. In addition, in some cases, the label also imparts a charge to the labeled carbohydrate. Exemplary labels include fluorophores, chromophores, radioisotopes, amperometric labels, chemiluminescent species, spin labels, and the like.

The term "differential label" as used herein refers to a label which is distinguishable from a label which is attached to a sample carbohydrate.

As used herein, the term "electrophoresis" or "electrophoretic migration" refers to the net migration of a solute under the influence of an electric field by the combined effects of electroosmosis and electrophoresis.

The term "capillary" as used herein refers to a tube or a channel or other structure capable of supporting a volume of separation medium for carrying out electrophoresis. The geometry of a capillary may vary widely and includes tubes with circular, rectangular, or square cross-sections, channels, grooves, plates, and the like and may be fabricated by a wide range of technologies. An important feature of a capillary for use with the invention is the surface-to-volume ratio of the surface in contact with the electrophoretic separation medium. High values of this ratio permit better heat transfer from the separation medium to the surroundings during electrophoresis. Preferably, values in the range of about 0.4 $\mu m^{-1}$ to 0.04 $\mu m^{-1}$ are employed. These correspond to the surface-to-volume ratios of tubular capillaries with circular cross-sections having inside diameters in the range of about 10 $\mu m$ to about 100 $\mu m$. In some cases, the inside surface of the capillary may be chemically modified in order to optimize its surface properties. Preferably, capillaries for use with the invention are made of silica, fused silica, quartz, silicate-based glass, such as borosilicate glass, phosphate glass, alumina-containing glass, and the like, or polymeric materials such as polytetrafluroethylene (Teflon™), polyethylene, and the like.

As used herein, the term "separation path" refers to the path taken by the sample between the inlet of the first separation capillary and the outlet of the last separation capillary.

The term "supplementary reagent" as used herein refers to any chemical species, or collection of chemical species, which is combined with the sample to facilitate the characterization of the sample, e.g., an internal standard, an enzyme, a selective binding reagent such as an antibody or a lectin, and the like.

As used herein, the term "selectivity" refers to the degree to which closely related carbohydrates can be distinguished based on their electrophoretic migration properties.

The term "effective length" as used herein refers to the length of capillary which is used for the separation, i.e., the length of capillary between the inlet and the detection regions of the capillary

II. DESCRIPTION OF APPARATUS

FIG. 1 shows a preferred embodiment of the carbohydrate analyzer of the present invention. First capillary (56) and second capillary (116) are connected through transfer cell (80) such that sample can travel from first capillary (56) to second capillary (116). In addition, transfer cell (80) connects first capillary (56) and second capillary (116) with inlet-transfer tube (84) and outlet-transfer tube (76). Both first (56) and second (116) capillaries are filled with a first and second separation medium. Injection autosampler (8) allows different solutions to be automatically presented to inlet end (20) of first capillary (56), e.g., first separation medium, sample solution, wash solutions, supplementary reagents, and the like. First transfer solution (108), located in first transfer reservoir (112), is connected to transfer cell (80) through inlet-transfer tube (84). Transfer autosampler (68) allows for a variety of reagents to be automatically presented to inlet end (86) of transfer tube (84), e.g., second separation medium, wash solutions, supplementary reagents, and the like. Outlet transfer reservoir (44) containing outlet transfer solution (48) is connected to transfer cell (80) through outlet-transfer tube (76). Typically, outlet transfer solution (48) is a waste solution. Outlet end (129) of second capillary (116) is immersed in second separation medium (128) located in second buffer reservoir (132). Outlet autosampler (105) allows different solutions to be automatically presented to outlet end (129) of second capillary (116), e.g. second separation medium, wash solutions, and the like. Each of the reservoirs described above is a sealable vessel and is connected to valve manifold (150) by atmosphere control lines (155), (160), (165), or (170). Valve manifold (150) provides a vent position, (VT), a vacuum position, (VM), and a pressure position, (P), for each atmosphere control line, such that the headspace pressure in each vessel can be independently controlled. Two power supplies provided to furnish the electrical potential required to drive the electrophoresis process: first power supply (60) provides an electrical potential between inlet end (20) of first capillary (56) and inlet end (86) of transfer tube (84), and second power supply (92) provides an electrical potential between inlet end (86) of transfer tube (84) and outlet end (129) of second capillary (116). The two power supplies may also be used in combination to create a potential between inlet end (20) of first capillary (56) and outlet end (129) of second capillary (116). Two detectors are provided to detect the sample bands during electrophoresis: first detector (52) detects sample bands subsequent to separation in first capillary (56), and second detector (88) detects sample bands subsequent to separation in second capillary (116). Detectors (52) and (88) are positioned near the terminal end of their respective capillaries so that detection takes place when the sample components are maximally separated. Note that first detector (52) and second detector (88) could be part of a single detector apparatus, e.g., a single detector having multiple flow cell locations. Detectors (52) and (88) may be connected to signal processing means(not shown in figure) for interpretation of the data produced by the detectors, e.g., a programmable computer.

It is preferred that first capillary (56) and second capillary (116) have, (i) a small internal diameter to provide a high external-surface-area-to-internal-volume ratio to facilitate efficient heat transfer, (ii) a wall thickness that permits the capillary to be flexible and be generally manipulated without breaking, and, (iii) be made from a material that allows detection through the capillary wall. The small internal diameter and resulting high external-surface-area-to-internal-volume ratio result in efficient heat transfer of Joule heat, thereby allowing the use of high electrical fields, leading to narrow sample bands and short analysis times. Preferably, capillaries (56) and (116) have a cylindrical cross-section, are made from fused silica, have an internal diameter of between 20 $\mu m$ and 200 $\mu m$, and have an external surface which is coated with a polymer coating to impart enhanced durability to the capillary, e.g. polyimmide, polytetrafluroethylene (Teflon™), and the like. Preferably, each capillary includes a detection region wherein the external coating is removed to facilitate transmission of light. More preferably, the detection region is located proximate to the outlet end of the capillary, where, as used herein, the term proximate refers to a location at least 70 percent of the distance from the inlet end to the outlet end of the capillary. The preferred internal diameter of first capillary (56) and second capillary (116) is between 10 μm and 200 μm, and more preferably between 25 μm and 100 μm. The effective length of capillaries (56) and (116) is dictated by the quality of separation required: the longer the effective length of the capillary the more complete the separation. More specifically, in most applications, resolution increases with the one-half power of the capillary effective length, i.e., by doubling the effective length, resolution is increased by a factor of 1.4. However, as the capillaries are made longer, the analysis time increases. Therefore, to balance the considerations of resolution and analysis time, the preferred capillary length is between 10 cm and 200 cm, more preferably between 25 cm and 100 cm.

An important aspect of the present invention is the transfer cell. Preferably, transfer cell (80) should provide for the transfer of sample from first capillary (56) to second capillary (116) with a minimum of sample loss or increase in bandwidth, particularly when different separation medium is present in each capillary. More preferably, transfer cell (80) should allow the delivery of a supplementary reagent into the electrophoretic separation path without perturbing the sample bands.

Figure 2:
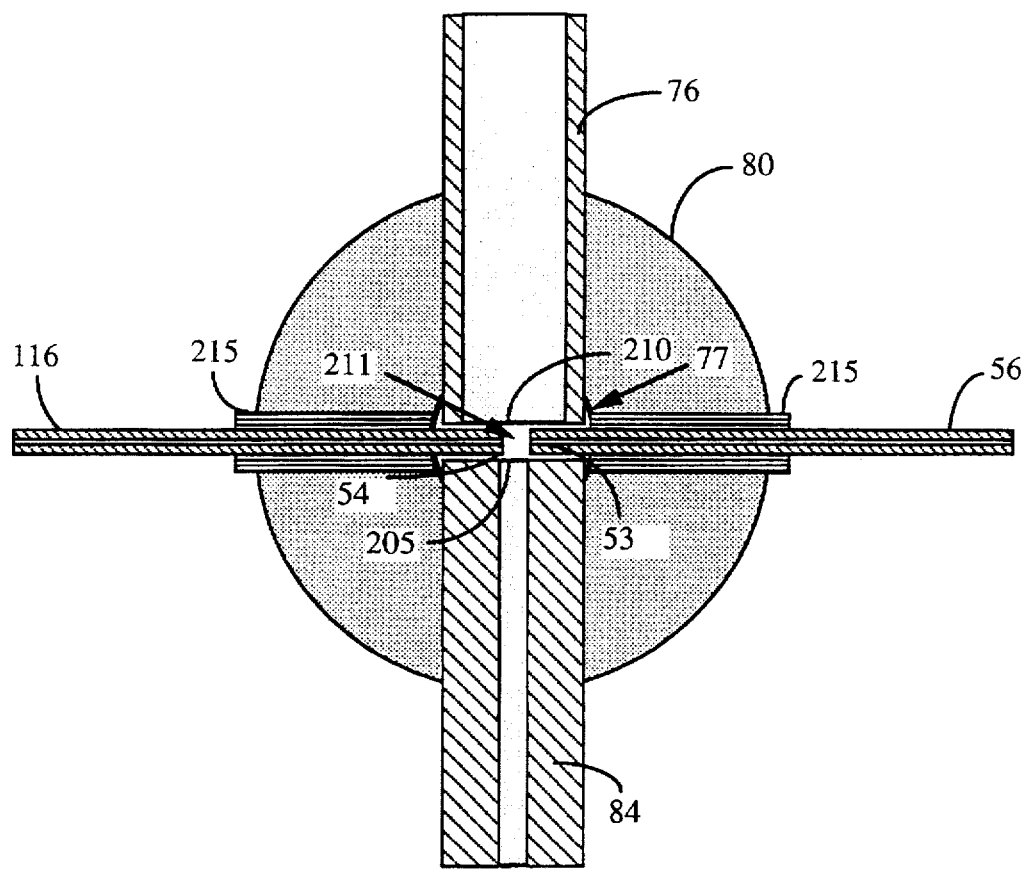
FIG. 2 is a schematic diagram of the transfer cell of the present invention.

The transfer cell herein described functions by holding first capillary (56) and second capillary (116) aligned with and in close proximity to each other and inlet-transfer tube (84) and outlet-transfer tube (76), e.g., Moring, U.S. Pat. No. 5,110,431. Preferably, transfer cell (80) is configured as in FIG. 2, wherein outlet end (53) of first capillary (56) and inlet end (54) of second capillary (116) are brought together in close proximity with outlet end (205) of inlet-transfer tube (84) and inlet end (210) of outlet-transfer tube (76) in gap volume (77). In order to maximize transfer efficiency, gap (211) must be optimized: if gap (211) is too small, free flow of ions and liquid through the gap is compromised, but, if gap (211) is too large, sample-peak width will be negatively affected. Preferably, gap (211) should be approximately equal to D/2, wherein D is the internal diameter of the smallest separation capillary. To ensure efficient transfer of sample across the gap, first capillary (56) and second capillary (54) must be precisely aligned. Preferably, the longitudinal axes of the capillaries are offset by less than D/2.

Figure 3:
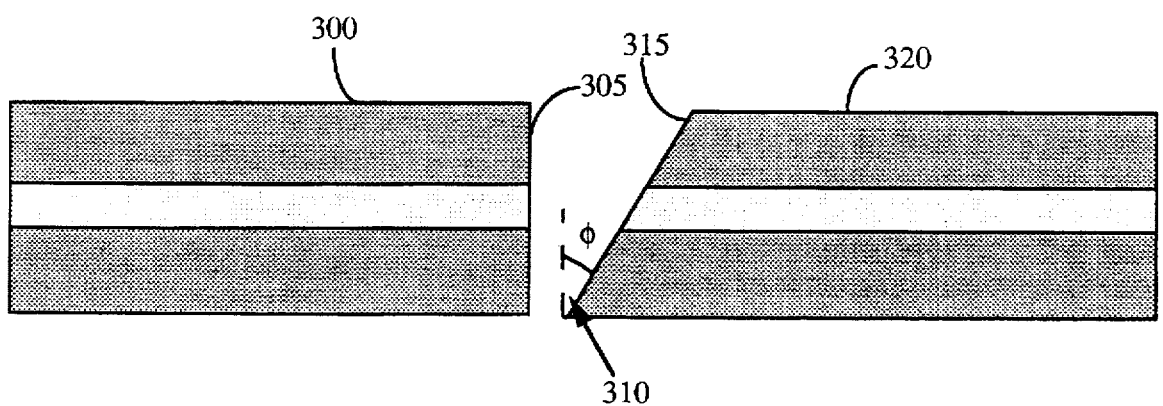
FIG. 3 is a schematic diagram of the gap between first and second capillaries formed by a preferred method of the invention FIG. 4A and B is an illustration of the effect of signal overlap on peak characterization.

A preferred method for forming gap (211) is to cut one of the capillaries with a flat face and the other with an angled, or beveled face; see FIG. 3. Face (305) of first capillary (300) is cut and polished such that it is flat. Face (315) of second capillary (320) is cut and polished such that it is angled at bevel angle (310) having a magnitude of φ. The preferred magnitude for φ is given by the expression, $\phi = \tan^{-1} (d/D)$ where d and D are the internal diameter and external diameter, respectively, of second capillary (320). By forming the gap in this way, it is possible to reproducibly and precisely form the gap with well defined dimensions without having to resort to time consuming manual manipulations. Clearly, it makes no difference which of the two capillaries has the beveled face.

To maintain the proper alignment, it is preferred that first capillary (56) and second capillary (116) are mounted in transfer cell (80) using, a press-fit mounting. The press-fit mounting is achieved by placing deformable sleeve (215) around the outside of the portion of capillaries (56) and (116) mated with the transfer cell. Said sleeve serves to form a snug fit between capillaries (56) and (116) and the transfer cell. The preferred material for transfer cell (80) is chemically inert, electrically non-conducting, and optically clear, e.g., polycarbonate, polymethyl pentene, and the like. The preferred material for sleeve (215) is electrically non-conducting and deformable, e.g., polytetrafluroethylene (Teflon™), and the like.

To minimize the effect of reagent flow through inlet-transfer tube (84) and outlettransfer tube (76) on the performance of the electrophoretic separation, the relative flow resistances of the four channels should be properly balanced: the pressure rise in gap volume (77) should be minimized, and, the flow resistance across first (56) and second (116) capillaries should be higher than that across outlet-transfer tube (76), such that any pressure which builds up in gap volume (77) will cause flow through outlet-transfer tube (76) rather than through first (56) and second (116) capillaries. Because flow resistance is determined by the diameter and length of each channel, to minimize the pressure rise in gap volume (77), outlet-transfer tube (76) should have a large diameter and a small length relative to first (56) and second (116) capillaries. To further reduce the possibility for a pressure rise in gap volume (77), the diameter of inlet-transfer tube (84) should be less than that of outlet-transfer tube (76). Therefore, if $D_{84}$ is the internal diameter of inlettransfer tube (84), $D_{76}$ is the internal diameter of outlet-transfer tube (76), $D_{56}$ is the internal diameter of first capillary (56) and $D_{166}$ is the internal diameter of second capillary (116), preferably, $D_{76} > D_{84} >> D_{56} \approx D_{166}$. More preferably, $D_{76}/D_{84} > 2.0$, $D_{84}/D_{56} > 5.0$.

Injection autosampler (8), transfer autosampler (68) and outlet autosampler (105) should be capable of presenting a variety of different solution-containing vessels to the ends of first (56) and second (116) capillaries and inlet transfer tube (84), e.g., ABI 270A HT Capillary Electrophoresis System, Applied Biosystems Division of the Perkin Elmer Corporation, Foster City, Calif. These solutions can include alternative separation media, capillary conditioning solutions, internal standards, sample solutions, and the like. Preferably, autosamplers (8), (68) and (105) provide a pressure-tight seal for each vessel presented to the capillary or transfer tube to allow for accurate control of the head-space pressure inside each vial. More preferably, autosampers (8), (68) and (105) can accommodate a plurality of solution vials, each vial being independently addressable by automatic programmed operation. Injection autosampler (8), transfer autosampler (68) and outlet autosampler (105) can be three independent mechanisms, or alternatively, be sectors of a lesser number of mechanisms.

Preferably, each vessel which is connected to first capillary (56), second capillary (116), inlet-transfer tube (84) or outlet-transfer tube (76), is connected to valve manifold (150) which directs either positive pressure, vent, or vacuum to the head-space of each vessel. By independently controlling the pressure in the head-space of each vessel, the system is able to direct the flow of fluids between the reservoirs. Preferably, valve manifold (150) is capable of controlling both vacuum and positive pressure and is electrically activated such that it can be controlled by computer. Preferably, the gas used to pressurize the vessels is minimally soluble in aqueous solutions, e.g., helium, argon, nitrogen, and the like. More preferably, the gas is helium.

First power supply (60) and second power supply (92) are preferably capable of providing up to 30,000 V DC and currents up to 300 μA. More preferably, power supplies (60) and (92) are capable of independent automatic programmed operation.

First detector (52) and second detector (88) should be capable of distinguishing carbohydrates, or labeled carbohydrates, from the background. Examples of such detectors include UV absorbence detectors, radioactivity detectors, refractive index detectors, fluorescence detectors, chemiluminescent detectors, spin-label detectors, amperometric detectors, and the like. Preferably, the detectors are capable of distinguishing between multiple labels. In one preferred embodiment, detectors (52) and (88) are fluorescent detectors capable of distinguishing between multiple labels having different fluorescence-emission wavelengths. First (52) and second (80) detectors can either be independent detectors or different detection zones of a single detector mechanism.

Preferably, the signal processing means should be capable of collecting the output of each detector, typically a time-varying electrical voltage or current, at a sufficient rate to define the electrophoretic peaks, e.g., an electronic computer programmed with a data collection system as is well know in the art. More preferably, the signal processing means should be capable of storing the collected detector output and comparing it with archived data resident in the memory of the signal processing means.

III. METHOD OF OPERATION

A. Sample Release and Derivatization

Most saccharides of interest are part of glycoconjugates, i.e., glycones of glycoconjugates, e.g., glycolipids, glycoproteins, and the like. Preferably, prior to analysis, the carbohydrate moiety is released. Applicable chemical methods include hydrazinolysis, borohydride cleavage, and the like. Enzymatic release can be used with glucoamidase, peptide N-glycosidase F, or various endoglycosidases. Glycolipids can be cleaved with endoglycoceramidase.

In many cases, it is preferable to derivatize the carbohydrate sample with a label prior to electrophoretic analysis. Because native carbohydrates are often uncharged and contain no readily detectable moieties, e.g., chromophores, fluorophores, chemiluminescent moieties, spin labels, and the like, electrophoretic separation and detection of carbohydrates can be problematic. By derivatizing the sample prior to electrophoresis with a label which includes a detectable moiety and is suitably charged under the conditions of electrophoresis, these problems can be largely overcome.

One preferred labeling method is based on reductive amination, wherein the reducing end of a carbohydrate reacts with the primary amino group of a label to form a Schiff base that is subsequently reduced to a secondary amine in the presence of cyanoborohydride or similar reductant, e.g., Prakash et al., Anal. Biochem., 128: 41–46 (1983), this reference being herein incorporated by reference. Preferably, labels used with this method include those shown in Table 1.

TABLE 1

Preferred Labels Which Can Be
Used With Reductive Amination Linking Chemistry 2-aminopyridine
p-aminobenzoic acid
ethyl p-aminobenzoic acid
p-aminobenzonitrile
2-aminoacridone
6-aminoquinoline
2-Aminobenzamide
7-aminonaphthalene-1,3-disulfonic acid (7-ANDA)
8-aminonaphthalene-1,3,6-trisulfonic acid (ANTS)
2-aminonaphthalene-1-sulfonic acid (2-ANSA)
3-aminonaphthalene-2,7-disulfonic acid (3-ANDA)

TABLE 1-continued

Preferred Labels Which Can Be
Used With Reductive Amination Linking Chemistry 4-aminonaphthalene-1-sulfonic acid (4-ANSA)
5-aminonaphthalene-2-sulfonic acid (5-ANSA)
8-aminonaphthalene-2-sulfonic acid (8-ANSA)
4-amino-5-hydroxy-2,7-naphthaline disulfonic acid
4-amino-3-hydroxy-1-naphthaline sulfonic acid
4-amino-5-hydroxy-1-naphthaline sulfonic acid
6-amino-4-hydroxy-1-naphthaline sulfonic acid
7-amino-4-hydroxy-1-naphthaline sulfonic acid
7-amino-4-methylcoumarin
7-amino-4-(trifluoromethyl)coumarin
FMOC-hydrazine
Dansyl-hydrazine
1-aminopyrene-3-6-8-trisulfonic acid (APTS)
1-pyrenyloxyacethydrazide-3-6-8-trisulfonic acid (Cascade Blue Hydrazide (CBH))
7-(5-amino-6-sulfo-2H-benzotriazol-2-yl)-1,3,6-naphthalenetrisulfonic acid
2-(4'-amino-3'-sulfo-4-biphenylyl)-2H-naphtho[1,2-d]triazole-6,8-disulfonic acid
2-(4-amino-3-sulfophenyl)-2H-naphtho[1,2-d]triazole-4,7,9-trisulfonic acid
7-amino-2-(p-sulfophenyl)-2H-naphtho[1,2-d]triazole-5,9-disulfonic acid
2-(m-aminophenyl)-2H-naphtho[1,2-d]triazole-5,7,9-trisulfonic acid
2-(4'-amino-3'-sulfo[1,1'-biphenyl]-4-yl)-2H-naphtho[1,2-d]triazole-6,8,-disulfonic acid
6-amino-2,3-dihydro-2-(4-methyl-3,5-disulfophenyl)-1,3-dioxo-1H-benz[de]isoquinoline-5,8-disulfonic acid, tripotassium salt
6-amino-2,3-dihydro-2-(4-methyl-3-sulfophenyl)-1,3-dioxo-1H-benz[de]isoquinoline-5,8-disulfonic acid, tetrapotassium salt
2-(4-amino-3-sulfophenyl)-2H-naphthol[1,2-d]triazole-4,7-disulfonic acid
3-amino-1,4,8-fluoranthenetrisulfonic acid, disodium salt
2-(4-aminophenyl)-2H-naphtho[2,3-d]triazole-4,6,9-trisulfonic acid
4-amino-9,10-dihydro-9,10-dioxo-1,3,5,8-anthracenetetrasulfonic acid, tetrasodium salt
5-amino-9,10-dihydro-9,10-dioxo-1,4,6-anthracenetrisulfonic acid, trisodium salt
5-amino-9,10-dihydro-9,10-dioxo-1,4,6-anthracenetrisulfonic acid A second preferred labeling method utilizes the fluorescent compound 3-(4-carboxybenzoyl)-2-quinolinecarboxaldehyde (CBQCA). In this method, fluorescent carbohydrate derivatives are obtained by reductive amination with ammonia, leading to 1-amino-deoxyalditols that are readily reacted with CBQCA in the presence of potassium cyanide, e.g., Liu, et al., Anal. Chem., 63: 408–412 (1991), this reference being herein incorporated by reference. A disadvantage of this procedure is that other amines present in the sample matrix, including those on the sample at positions other than the reducing end, may also be tagged and therefore interfere with the analysis. An additional disadvantage of this procedure is that it requires the use of toxic reagents, e.g., cyanide.

A third preferred labeling method involves the base catalyzed condensation of the carbonyl group of reducing carbohydrates and 1-phenyl-3-methyl-5-pyrazolone (PMP) or 1-(p-methoxy)phenyl-3-methyl-5-pyrazolone (PMPMP), yielding bis-PMP and bis-PMPMP derivatives, respectively, e.g., Honda et al., J. Chromatgr., 608:289–295 (1992), this reference being herein incorporated by reference. Since condensation occurs under slightly alkaline conditions (pH≅8.3), both PMP and PMPMP are well suited for labeling sialylated oligosaccharides because no loss of sialic acid residues occurs in this pH range. In addition, labeling with PMP or PMPMP does not require the use of strong reducing agents such as diborane dimethylamine or sodium cyanoborohydride, and avoids the use of toxic reagents such as 2-aminopyridine. A drawback of this labeling method is the chemical instability of both bis-PMP and bis-PMPMP.

A fourth preferred labeling method utilizes NHS-ester-containing dyes or isothiocyanate-containing dyes. These dyes can be attached to sugars by first forming an amine moiety directly on the reducing end of the sugar then reacting a NHS-dye with the aminated carbohydrate using standard methods, e.g., Liu et al., Proc.Natl.Acad.Sci., 88: 2302–2306 (1991), Zhao, et al., Glycobiology, 4: 239–242 (1994), these references being herein incorporated by reference.

B. Multi-Dimensional Capillary Electrophoresis Separation

1. Sample Introduction: Sample is introduced into first capillary (56) by either a hydrodynamic or an electrokinetic injection method. In electrokinetic injection, sample is introduced into the capillary by applying a voltage across the capillary while the inlet end of the capillary is immersed in the sample, wherein the polarity of the voltage is chosen such that, under the electrophoresis conditions used, the sample migrates into the capillary. Preferably, electrokinetic injection is accomplished by first immersing inlet end (20) of first capillary (56) and first electrode (22) into the sample while outlet end (86) of transfer cell-feed tube (84) and second electrode (87) are immersed in a separation medium. Both reservoirs (18) and (112) are vented to atmosphere during electrokinetic injection. Next, an injection voltage is established across first capillary (56), by means of first electrical power supply (60) electrically connected to electrodes (22) and (87), for a selected injection time, after which inlet end (20) of first capillary (56), and electrode (22) are removed from the sample solution and placed in a reservoir containing electrophoretic separation medium. In a preferred electrokinetic injection method, a voltage of between 1 and 5 kV is applied between resevoirs (18) and (86) for an injection time of between 2 and 10 s.

In hydrodynamic injection, sample is introduced into the capillary by applying a pressure difference across the capillary while the inlet end of the capillary, i.e. the high-pressure end, is immersed in the sample. Preferably, in the present analyzer, hydrodynamic injection is accomplished by first immersing inlet end (20) of first capillary (56) into the sample, while outlet end (86) of transfer tube (84) is immersed in a separation medium. A pressure difference is then applied across first capillary (56) for a specified injection time, after which inlet end (20) of first capillary (56), and first electrode (22) are removed from the sample and placed in a reservoir containing electrophoretic separation medium. In a preferred method, a vacuum of 2.5 psi is applied to resevoirs (112), (44), and (132) while vessel (18) is vented to atmosphere for an injection time of 2 s.

2. Electrophoretic Separation: Once sample has been introduced into first capillary (56), the first "dimension" of the electrophoresis is performed by applying voltage across first capillary (56). During the first dimension electrophoresis, transfer tube (84) and first transfer reservoir (112) are filled with the first separation medium. The polarity of the electrophoresis voltage and electrophoresis conditions are chosen such that the sample migrates towards transfer cell (80). A preferred electrophoresis voltage is between 5 kV and 30 kV. Sample bands are detected by first detector (52) located at the end region of first capillary (56). Similarly, with respect to the second dimension electrophoresis, once the sample band has been transferred across transfer cell (80), the second dimension electrophoresis is carried out in substantially the same manner as the first. However, this time the voltage polarity and the separation medium conditions are chosen such that the sample migrates away from transfer cell (80).

A variety of different electrophoretic separation modes may be used with the present invention: free solution capillary electrophoresis (FSCE), micellar electrokinetic capillary chromatography (MECC), isoelectric focusing (IEF), and sieving-based separations using either cross-linked gels or semi-dilute polymer solutions. The principles underlying each of these separation modes are described elsewhere, e.g., Grossman et al., editors, Capillary Electrophoresis (Academic Press, San Diego, Calif. 1992). It is an important aspect of the present invention that multiple separation modes can be performed serially in an automated fashion. By performing, multiple separation steps which rely on different structural features of the sample to discriminate between related species, it is possible to greatly enhance the combined resolving power of the analysis. This enhanced resolving power can even be realized using a single mode by using two different operating conditions, e.g., a FSCE separation at two different pH values and/or buffer compositions. A preferred buffer combination for 2-D FSCE separations of carbohydrates is 36 mM triethylamine, 50 mM phosphate at pH 2.5 in the first dimension and 250 mM boric acid titrated with sodium hydroxide to pH 8.5 in the second dimension.

3. Intercapillary Transfer: An important aspect of the present invention is the ability to transfer a selected sample band from a first capillary to a second capillary during an electrophoretic separation such that little or no sample is lost and the width of the sample band is not significantly increased. If sample mass were lost in the transfer, accurate quantitation of the sample would be difficult, and, if the width of the sample peak were increased, overall resolution would be impaired. There are three methods which can be used to perform the intercapillary transfer of a selected sample band: an electrokinetic transfer method, a hydrodynamic transfer method, and a hybrid transfer method using both electrokinetic and hydrodynamic means. Preferably, hydrodynamic transfer is accomplished as follows. When the selected sample band is detected by first detector (52), a "delay time" is calculated to determine when the selected peak will arrive at the outlet end of first capillary (56). The delay time, $t_d$, is calculated based on the distance between inlet end (20) and first detector (52) of first capillary (56), $L_{det}$, the time required for the sample peak to travel that distance, $t_{det}$, and the distance between first detector (52) and transfer cell (80), $L_{gap}$, such that $t_d=((L_{gap}*t_{det})/L_{det})$. Once the selected peak arrives at first detector (52), electrophoresis is continued until the delay time has elapsed, at which time the electrophoreis voltage is turned off, leaving the selected peak at the outlet end of first capillary (56) adjacent to transfer cell (80). (Note that by calculating the delay time in this way, it is assumed that the peak velocity is constant throughout first capillary (56).) If a second separation medium is used in second capillary (116), prior to transferring the sample band across transfer cell (80), the first separation medium in gap volume (77) is replaced by the second separation medium. This exchange is accomplished by removing inlet end (86) of transfer tube (84) from transfer vessel (112) containing the first separation medium, placing it in a second transfer vessel containing a second separation medium, and applying pressure, e.g., 5 psi, to the second transfer vessel while all other vessels are vented to atmosphere. Second separation medium is flushed through gap region (77) long enough to replace first separation medium with second separation medium, e.g., for less than 1 min. Once the separation medium is exchanged, electrophoresis in second capillary (116) can proceed. To transfer the sample band across gap (211), vacuum is applied to second buffer reservoir (132) and pressure is applied to first buffer reservoir (18) while all other reservoirs are vented to atmosphere. The differential pressure is applied for only a few seconds; long enough to sweep the sample band across transfer cell (80) into the entrance region of second capillary (116). If differential pressure is applied longer than is necessary, significant band broadening can occur due to the parabolic laminar flow profile of the pressure-driven flow.

Preferably, to perform electrokinetic transfer of a sample peak from a first capillary to a second capillary, the following steps are performed. First, the sample band is positioned at the end of first capillary (56) using the delay-time method , and, if a second separation medium is used, the first separation medium is expelled from the transfer cell and replaced by the second separation medium. Next, electrophoresis is simultaneously performed in first capillary (56) and second capillary (116) for long enough to expel the sample band from first capillary (56) and introduce it into second capillary (116); typically a period of one to ten seconds. Preferably, the simultaneous electrophoresis is carried Out by placing transfer cell (80) at approximately ground potential, while the voltages and separation medium conditions in first (56) and second (116) capillaries are chosen such that, in first capillary (56), the sample migrates toward transfer cell (80), while in second capillary (116), the sample migrates away from transfer cell (80).

Preferably, to perform a hybrid electrokinetic-hydrodynamic transfer of a sample peak from a first capillary to a second capillary, the following steps are performed. First, the sample band is positioned at the end of first capillary (56) using the previously described delay-time method , and, if a second separation medium is used, the first separation medium is expelled from the transfer cell and replaced by the second separation medium. Next, the steps described above for the hydrodynamic transfer method and the electrokinetic transfer method are performed simultaneously, i.e., during the transfer step, the sample band is expelled from the first capillary electrokinetically by applying the appropriate voltage, and, it is drawn into the second capillary hydrodynamically by applying a vacuum to the second buffer reservoir. Alternatively, the sample is expelled from the first capillary hydrodynamically and is drawn into the second capillary electrophoretically.

As an alternative to the delay-time method for selecting material to be transferred between capillaries, selection can be effected by periodically transferring an aliquot of the contents of the first capillary at predetermined, regular, intervals. Using this method, at regular intervals, the first electrophoresis is stopped, and if necessary, buffer in the transfer cell is exchanged, sample is transferred, the second electrophoresis is started, then, once the second electrophoresis has proceeded sufficiently, the sampling process is repeated. Using this method may result in many more transfer steps, but, it eliminates the need for a first detector and a delay time calculation.

C. Introduction of a Supplementary Reagent at the Transfer Cell

There exist a number of situations in which it is advantageous to introduce a supplementary reagent into the separation path between the first and second electrophoretic dimensions. Examples include (i) the introduction of an internal standard into the second electrophoretic dimension, (ii) the introduction of structure-specific enzymes, and, (iii) the introduction of a specific binding reagent which specifically interacts with certain carbohydrate structures, e.g., lectins or antibodies. Each of these operations requires the ability to introduce a reagent into the separation path between first capillary (56) and second capillary (116) while not compromising the quality of the electrophoretic separation.

To introduce a supplementary reagent into the separation path at the transfer cell, once the selected sample band has been located at the tip of first capillary (56) the first electrophoresis is stopped, and a first transfer cell feed reservoir containing a first separation medium is replaced by a second transfer cell feed reservoir containing a desired supplementary reagent. Next, the second transfer cell feed reservoir is pressurized for a selected time, e.g., 5 psi for 5 s, while all other vessels are vented to atmosphere, thereby causing the contents of the second transfer cell feed reservoir to flow through transfer tube (84) into gap volume (77) of transfer cell (80), filling gap volume (77). Next, the sample band is transferred from first capillary (56) into second capillary (116) using any of the above described methods, i.e., using a hydrodynamic, electrokinetic, or hybrid transfer means. During the transfer, a portion of the supplementary reagent is swept into second capillary (116) along with the sample, thereby mixing the reagent with the sample peak. The supplementary reagent is then flushed out of gap volume (77) and replaced by the second dimension electrophoretic separation medium by pressurizing a transfer cell feed reservoir containing the second separation medium for a specified time, e.g. 5 psi for 5 s, while all other vessels are vented to atmosphere. Finally, the second dimension electrophoresis is started by turning on second power supply (92).

One preferred method utilizing the reagent-addition feature of the present invention is automated carbohydrate sequencing. As now practiced, carbohydrate sequencing is performed by dividing a purified oligosaccharide sample into aliquots, reacting each aliquot with a defined mixture of enzyme reagents having known specificities, performing electrophoresis of the reaction products, and correlating the results of the electrophoresis with the known specificity of the enzyme mixture e.g., Edge, et al., Proc.Natl.Acad.Sci. USA, 89: 6338–6342 (1992), this reference being herein incorporated by reference. In the method of the present invention, a carbohydrate mixture is separated in a first CE dimension, a selected component is transferred to a second capillary along with the addition of selected enzyme reagents, the enzyme-sample mixture is allowed to incubate for a selected time, and the mixture is electrophoresed in a second CE dimension, preferably using the same separation medium and conditions as used in the first dimension. The shift in electrophoretic mobility of the selected component between the first and second CE dimensions is then correlated with the known activity of the particular enzyme reagent used. The process is then repeated, using different enzyme reagents in each cycle. By repeating this series of steps, each component in a carbohydrate mixture can be sequenced without any manual intervention. An advantage of this technique over existing methods is that it does not require a pre-purified sample; the first CE dimension serves to automatically "purify" the sample material prior to treatment with the enzyme reagent. Furthermore, the process is totally automated. Preferred exoglycosidase enzymes which can be used in this method include, bovine epididymal α-L-fucosidase, jack bean β-galactosidase, jack bean β-N-acetylhexosaminidase, *Diplococcus pneumoniae* β-N-acetylhexosaminidase, jack bean α-mannosidase, *achatina fulica* β-mannosidase, almond meal α¾-L-fucosidase, *Charonia lampas* α-L-fucosidase, and the like, e.g., Edge, et al., Proc.Natl.Acad.Sci. USA, 89: 6338–6342 (1992), this reference being herein incorporated by reference.

D. Utilization of Multi-Color Detection Methods

1. Differentially-Detectable Internal Standards used with Mapping and Sequencing The basis of electrophoretic mapping techniques is the comparison of the electrophoretic profile of an unknown sample with that of one or more pre-characterized species, e.g., oligosaccharides whose structure has been conclusively determined by nuclear magnetic resonance and mass spectroscopy. The structure of the sample can be inferred by comparing the elution time of the sample with that of the pre-characterized species, while the quantity of the sample injected is indicated by the height and area of the sample peak. The quality of these comparisons can be compromised by the inherent variability in the electrophoresis operating conditions, e.g., temperature, electrical field strength, injection time, and the like. These uncertainties can be reduced by using an "internal standard", wherein the migration time, peak area, and peak height of the sample are normalized with respect to the internal standard.

Figure 4A:
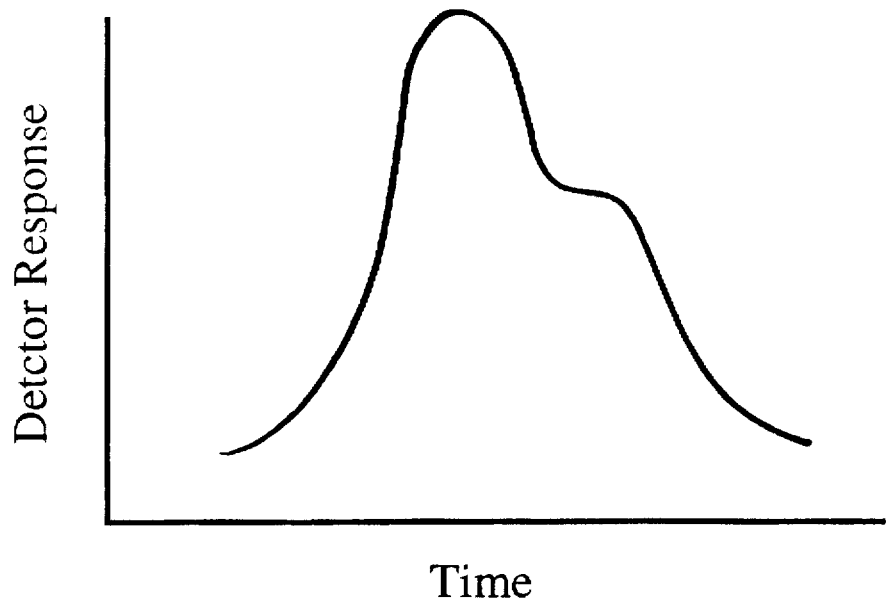

While the use of an internal standard provides several important advantages, an important shortcoming remains: the elution profile of the sample peak can be confused with and/or obscured by the elution profile of the standard, thereby complicating the task of determining the elution time, width, and height of the sample peak. For example, if the elution profile of the sample and the standard overlap, as in FIG. 4A, it is impossible to accurately determine which features of the elution profile are attributable to the standard and which are attributable to the sample. This problem can be particularly severe in cases where both the sample and the standard are composed of a plurality of resolvable species.

Figure 4B:
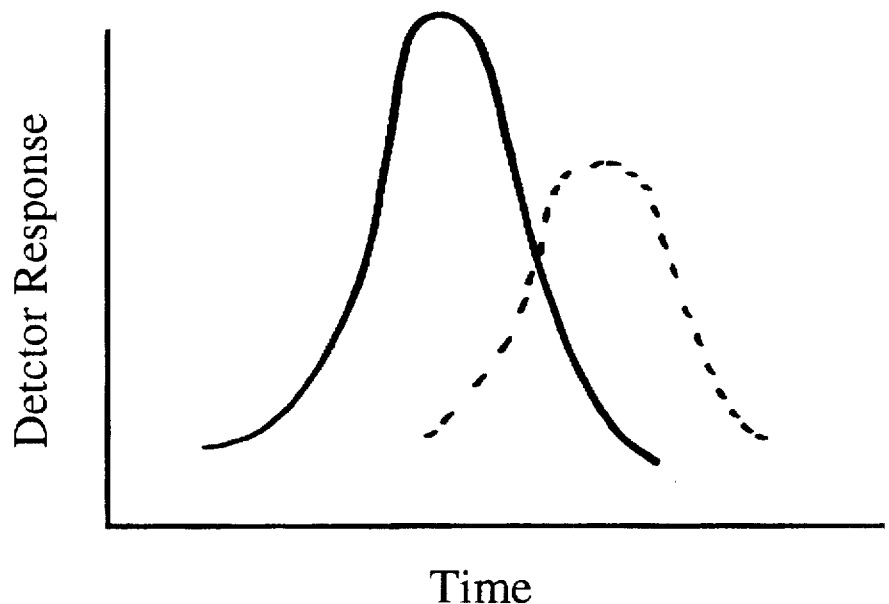

An important aspect of the present invention is the realization that by labeling the sample and the standard with differentially detectable labels, the problems associated with interference by the internal standard profile with the sample profile can be largely eliminated. When the sample and the standard are differentially labeled, as shown in FIG. 4B, the elution profiles of the sample and the standard are independent of each other, making it possible to more clearly identify each peak.

One preferred embodiment of the present invention employs multiple spectrally resolvable fluorescent labels. Preferably, fluorescent labels for use in the multi-color internal standard method of the invention should be spectrally resolvable from one another. One preferred dye combination is 2-amino-1-naphthalenesulfonic acid (2-ANSA) and 5-amino-2-naphthalenesulfonic acid (5-ANSA), wherein both labels are excited at 250 nm, and 2-ANSA fluorescence is detected at 400 nm and 5-ANSA fluorescence is detected at 520 nm. A second preferred dye combination is 4-amino-1-naphthalene sulfonic acid and 5-amino-2-naphthalenesulfonic acid, wherein both labels are excited at 250 nm, and 4-amino-1-naphthalenesulfonic acid fluorescence is detected at 400 nm while 5-amino-2-naphthalenesulfonic acid fluorescence is detected at 520 nm. A third preferred dye combination is 1-aminopyrene-3,6,8-trisulfonic acid and 1-pyrenyloxyacethydrazide, wherein the 1-aminopyrene-3,6,8-trisulfonic acid is preferably excited at 430 nm and emmission is preferably detected at 530 nm, and the and 1-pyrenyloxyacethydrazide is preferably excited at 376 nm and emmission is preferably detected at 436.

In some cases, in order to increase the selectivity of the mapping experiment, it is desirable to use multiple internal standards. For example, it might be advantageous to use an internal standard composed of a series of linear, biantennary, and triantennary oligosaccharides. In a single-label system, having multiple internal standards would compound the problem of establishing the identity and properties of each peak: not only would the sample peaks have to be distinguished from the internal standard peaks, but the peaks from one internal standard would have to be distinguished from those of other internal standards. However, by utilizing distinguishable labels on the sample and each of the standards, it is possible to incorporate multiple standards into the analysis without confounding data interpretation.

2. Multi-Enzyme Digestion using Differentially Detectable Labels

A further important aspect of the present invention is the application of multiple independently detectable labels in the context of enzymatic structural analysis of carbohydrates. In enzymatic structural analysis, the sample is treated with an ordered array of structure-specific enzymes, e.g., exo-and endoglycosidases, prior to an analytical separation step, e.g., Edge et al., Proc. Nat. Acad. Sci. USA, 89: 6338–6342 (1992). Preferably, the sample is divided into several aliquots prior to digestion, and each aliquot is treated with a different enzyme or enzyme cocktail. By noting the shift in migration time induced by each enzyme or enzyme cocktail, valuable structural information can be deduced.

In the present invention, sample in each aliquot is labeled with an independently detectable label. Subsequent to digestion, the aliquots are combined and are analyzed simultaneously using capillary electrophoresis as described above, wherein the products of each digestion are distinguishable by their associated label. By combining the samples prior to electrophoresis, fewer separation steps are required, leading to a faster analysis, and a single profile is created, eliminating the problems associated with reconciling the results of multiple separations. A differentially labeled standard may also be added to the sample.

3. Treatment with Differentially-Labeled Binding Reagents

In a further aspect of the present invention, the carbohydrate sample is treated with one or more specific binding reagents, e.g., antibody, lectin, and the like, either prior to the separation or between separation dimensions of a multi-dimensional separation process, wherein the binding agents are labeled with labels which are differentially detectable from the sample. Differentially labeling the binding agent simplifies the determination of whether and to what extent binding has occurred. Moreover, if multiple binding agents are used, by differentially labeling each binding agent, it is possible to determine which of the binding agents bound to each sample species.

IV. EXAMPLES

The following examples describe various aspects of the apparatus and methods of the carbohydrate mapping and sequencing system of the present invention. The examples are intended to illustrate, but not limit the scope of the invention.

EXAMPLE 1

Inter-Capillary Peak Transfer

This example describes the transfer of a sample peak from a first capillary to a second capillary of a 2-D capillary electrophoresis system using the electrokinetic transfer method.

The 2-D electrophoresis apparatus used in this example is essentially that described in Section II of the Detailed Description of the Invention section of this application. The system was configured in the following manner: the internal diameter of the cylindrical fused silica capillaries was 50 µm (Polymico Technologies, Tucson, AZ); the inside surface of the capillaries was uncoated bare silica; the outside surface of the capillaries was coated with polyimmide except at the detection region where, to allow efficient transmission of the excitation and emission light into and out of the capillary, the exterior polymer coating was removed from the capillary at the detection zone; the distance between the inlet and the detection zone of each capillary was 0.5 m; the overall length of the first and second capillaries was 0.53 m and 0.75 m, respectively; the first capillary and the first buffer reservoir contained a first separation medium composed of 36 mM triethylammonium phosphate, pH 2.5; the second capillary and the second buffer reservoir contained a second separation medium composed of 250 mM sodium borate, pH 8.5; electrophoresis was performed in both capillaries at a constant current of 15 µA; the electrodes at the inlet of the first capillary and the outlet of the second capillary were both at −12 kV while the electrode in the transfer cell feed reservoir was held at ground potential. No attempt was made to either control or measure the temperature of the capillaries during electrophoresis. The inlet and outlet transfer tubes were each 30 cm long having internal diameters of 300 µm and 800 µm, respectively.

The sample mixture was a 6 mg/mil aqueous solution of a standard M-150 maltodextrin carbohydrate ladder (Grain Processing Corporation, Muscatine, IA) labeled with 4-aminonaphthalene-1-sulfonic acid and diluted in water.

Figure 5:
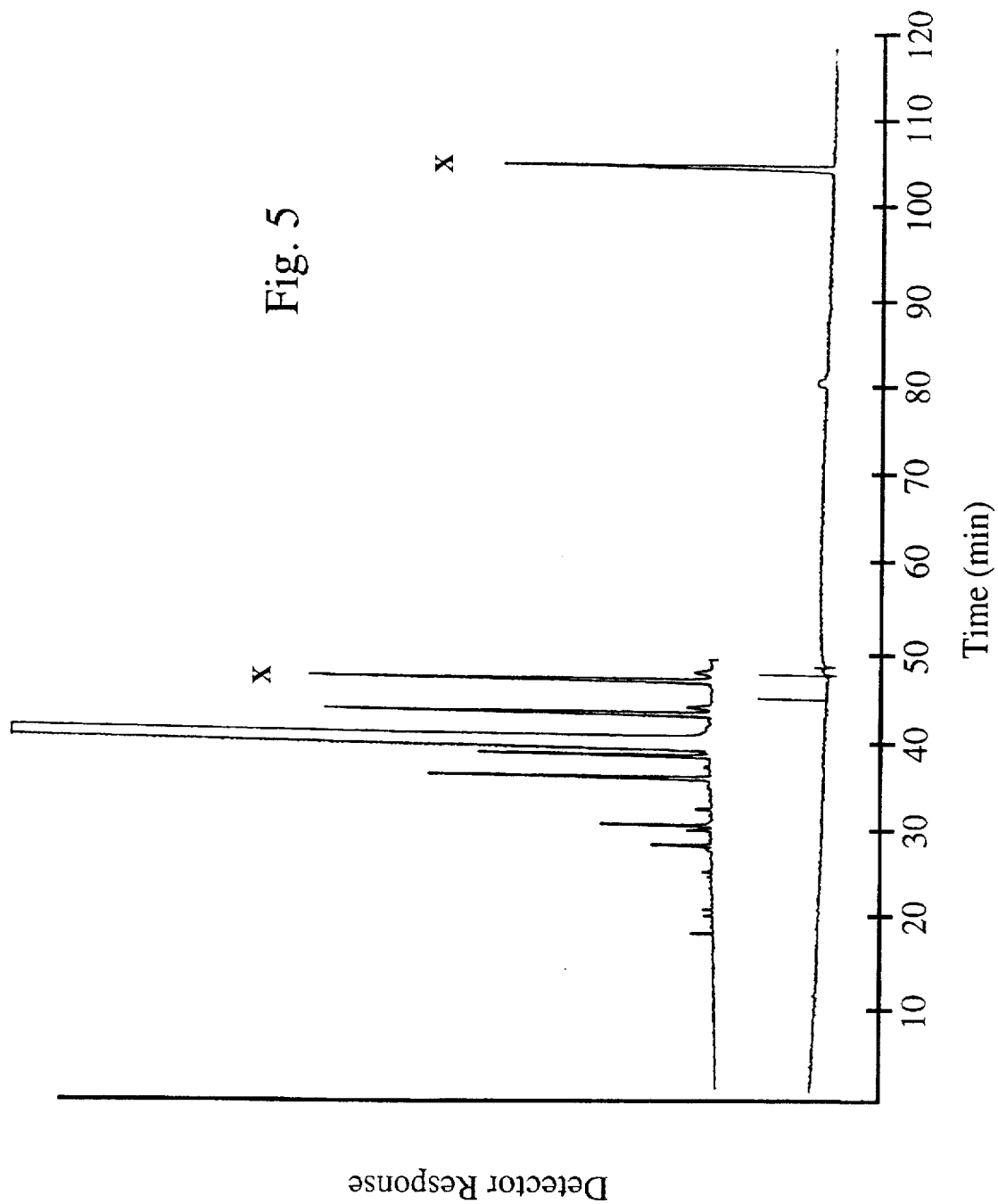
FIG. 5 is an example showing the transfer of a selected sample peak between two CE capillaries connected by a transfer cell according to the present invention.

To ensure that both capillaries were filled with their respective separation media, the first and second buffer reservoirs were pressurized to 5 psi for 5 min while all other reservoirs were vented to atmosphere. To fill the transfer cell with buffer, the transfer cell feed reservoir was filled with the first separation medium and pressurized at 5 psi for 5 s while all other vessels were vented to atmosphere. Sample was injected into the first capillary by exchanging the first buffer reservoir with a vial containing the sample, immersing the first capillary in the sample, and applying 5 inches of mercury vacuum for 2 s to all vessels except the sample vial. The sample vial was then replaced by the first buffer reservoir containing the first separation medium. Following sample injection, the first power supply was turned on and data collection was started. When the peak of interest appeared at the first detection region, Peak X in FIG. 5 (top), a delay time was calculated and, after the delay time had elapsed, the first power supply was turned off, leaving the selected peak at the tip of the outlet end of the first capillary. Following the first electrophoresis, the first separation medium in the transfer cell was replaced by the second separation medium by removing the first transfer cell feed reservoir and replacing it with a second transfer cell feed reservoir containing the second separation medium and pressurizing the second transfer cell feed reservoir at 5 psi for 2 s while all other vessels were vented to atmosphere. To transfer the selected peak across the transfer cell, both the first and second power supplies were turned on for a period of one peak width, or approximately 5 s. Finally, the second power supply was turned on and the second electrophoresis was performed. FIG. 5 shows the results of the described experiment wherein the top trace shows the results from the first dimension electrophoresis and the bottom trace shows the results from the second dimension electrophoresis, wherein Peak X in the first dimension was selected and transferred from the first capillary to the second capillary.

EXAMPLE 2

Intercapillary Peak Transfer with Simultaneous Internal Standard Addition

This example describes the transfer of a sample peak from a first capillary to a second capillary with the simultaneous addition of an internal standard.

The apparatus configuration, buffers, electrophoresis operating conditions, capillary preparation, sample injection, first electrophoresis, and delay time measurement used in this example were the same as those used in Example 1.

Following the first electrophoresis, the internal standard was introduced into the separation path by pressurizing the transfer cell feed reservoir containing an internal standard dissolved in second separation medium at 5 psi for 2 s while all other vessels were vented to atmosphere. To transfer the selected peak across the transfer cell, both the first and second power supplies were turned on for a period of one peak width, or approximately 5 s. Next, the transfer cell feed reservoir containing the standard was replaced by one containing only second separation medium, and the transfer cell was flushed with second separation medium. Finally, the second power supply was turned on and the second electrophoresis was performed.

FIG. 6 shows the results of the above described experiment where the top trace shows the results from the first dimension electrophoresis and the bottom trace shows the results from the second dimension electrophoresis, wherein Peak X in the first dimension was selected and transferred from the first capillary to the second capillary and an internal standard was added through the transfer cell. Peaks 1, 2, and 4 in both the bottom and top traces are the standard components having sizes of 1, 2, and 4 glucose units.

EXAMPLE 3

Use of Differentially-Labeled Internal Standard

This example describes the differential detection of a sample peak and an internal standard using multi-color fluorescence detection.

The electrophoresis system used in this example was a modified Applied Biosystems Model 270A capillary electrophoresis instrument (Applied Biosystems Division of the Perkin Elmer Corporation, Foster City, Calif.) which had been configured to perform multi-color fluorescence detection. The electrophoresis system was configured in the following manner a single uncoated 50 µm internal diameter capillary having a total length of 72 cm and a separation path length of 50 cm was installed; the separation medium consisted of 36 mM triethylammonium phosphate, pH 2.5; sample was injected by hydrodynamic injection using a 5 psi vacuum applied for between 1 and 2 s; the electrophoresis voltage was 20 kV (cathode at the inlet end of the capillary) resulting in a current of between 15 and 19 µA at the operating temperature of between 25° and 30° C.

Generally, the fluorescence detection system was configured as follows. Excitation light (EX) having a wavelength of 250, 376 or 430 nm was selected from the output of a deuterium lamp using a 7 nm bandpass monochrometer, then directed through a sapphire ball lens located adjacent to the outside wall of the separation capillary. To allow efficient transmission of the excitation and emission light into and out of the capillary, the exterior polymer coating was removed from the capillary at the detection zone. Depending on the analyte, emission light (EM) was passed through either a 400, 436, 520, or 530 nm bandpass filter, each filter having a transmission band width of 10 nm, then detected using a photomultiplier tube. The photomultiplier output was directed directly to a strip-chart recorder.

Sample-internal standard mixtures were prepared by adding 1 µl standard (M-150 maltodextrin ladder or M-040 maltodextrin ladder ((both from Grain Processing Corporation, Muscatine, IA), 120 mg/ml in 17:3:20 water-:acetic acid:DMSO) and between 2 and 4 μl sample (10–50 nmol in 17:3:20 water:acetic acid:DMSO) to between 6 and 10 μl water.

Each 2-color experiment was carried out by performing two separate runs of the same sample-internal standard mixture wherein the emission filter was changed between each run. The top trace in each panel shows the sample-internal standard mixture detected at a first wavelength while the bottom shows the sample-internal standard mixture detected at a second wavelength. The large early peak in each of the electropherograms is due to unreacted labeling reagent.

Figure 7A:
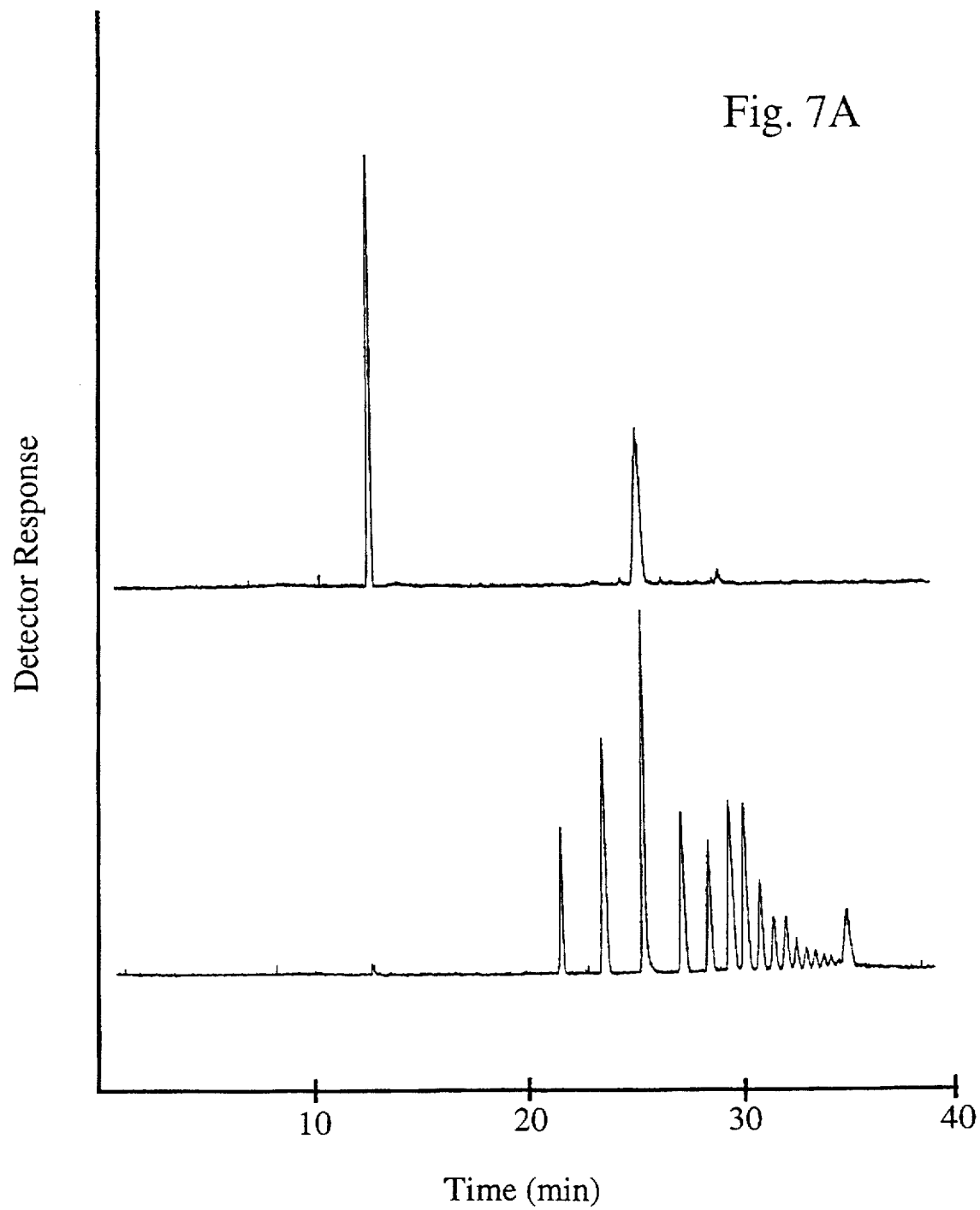
Figure 7C:
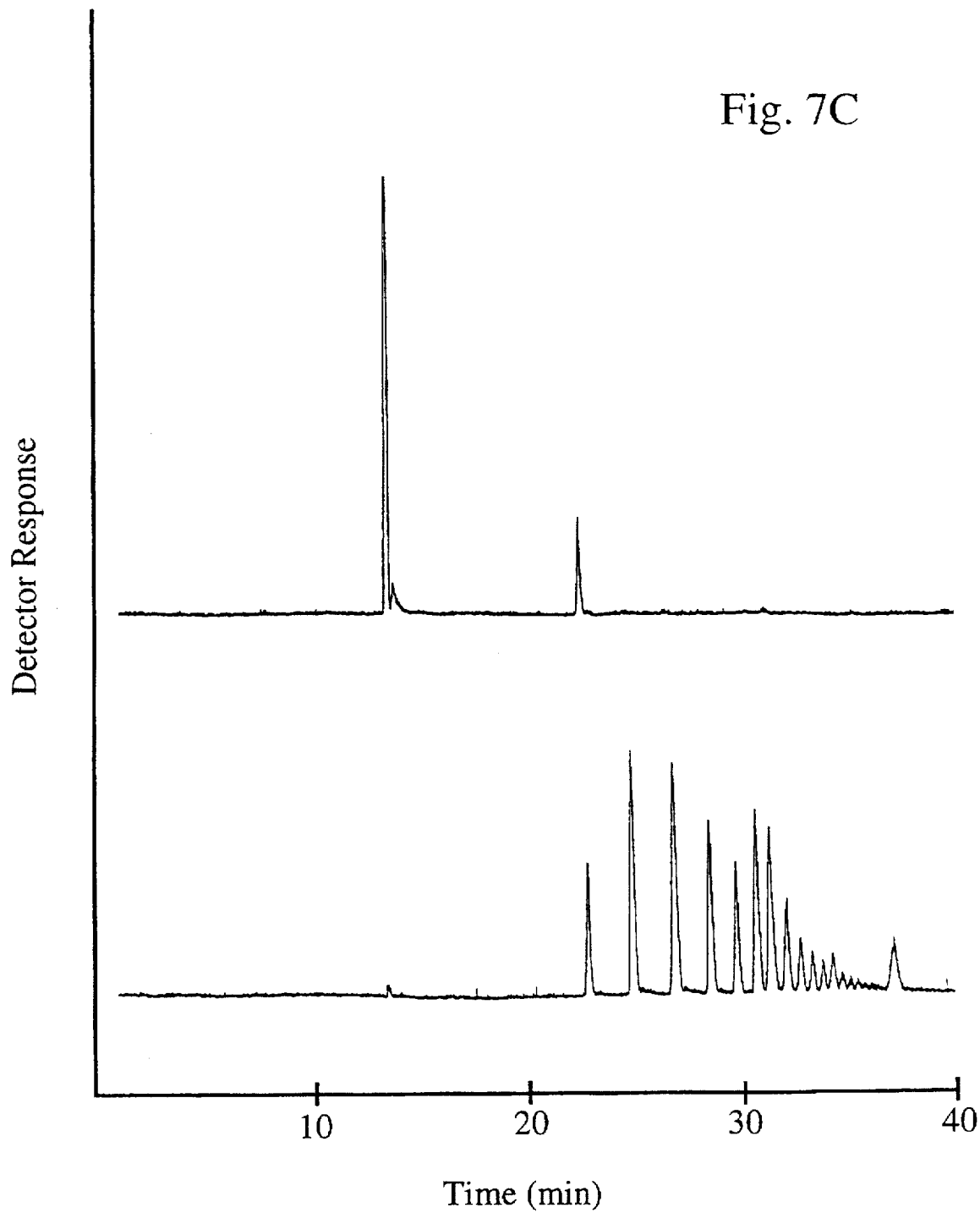
Figure 7D:
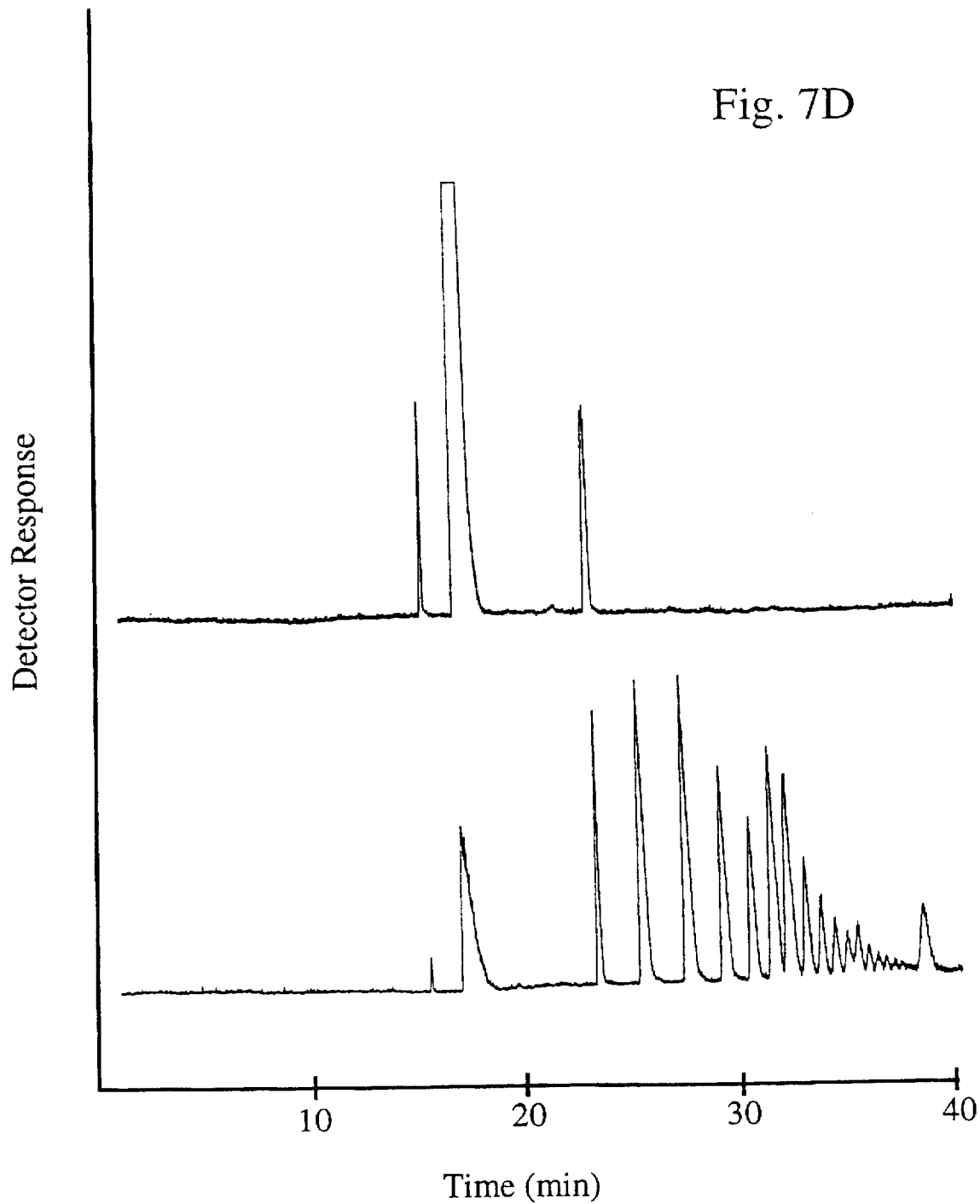
Figure 7E:
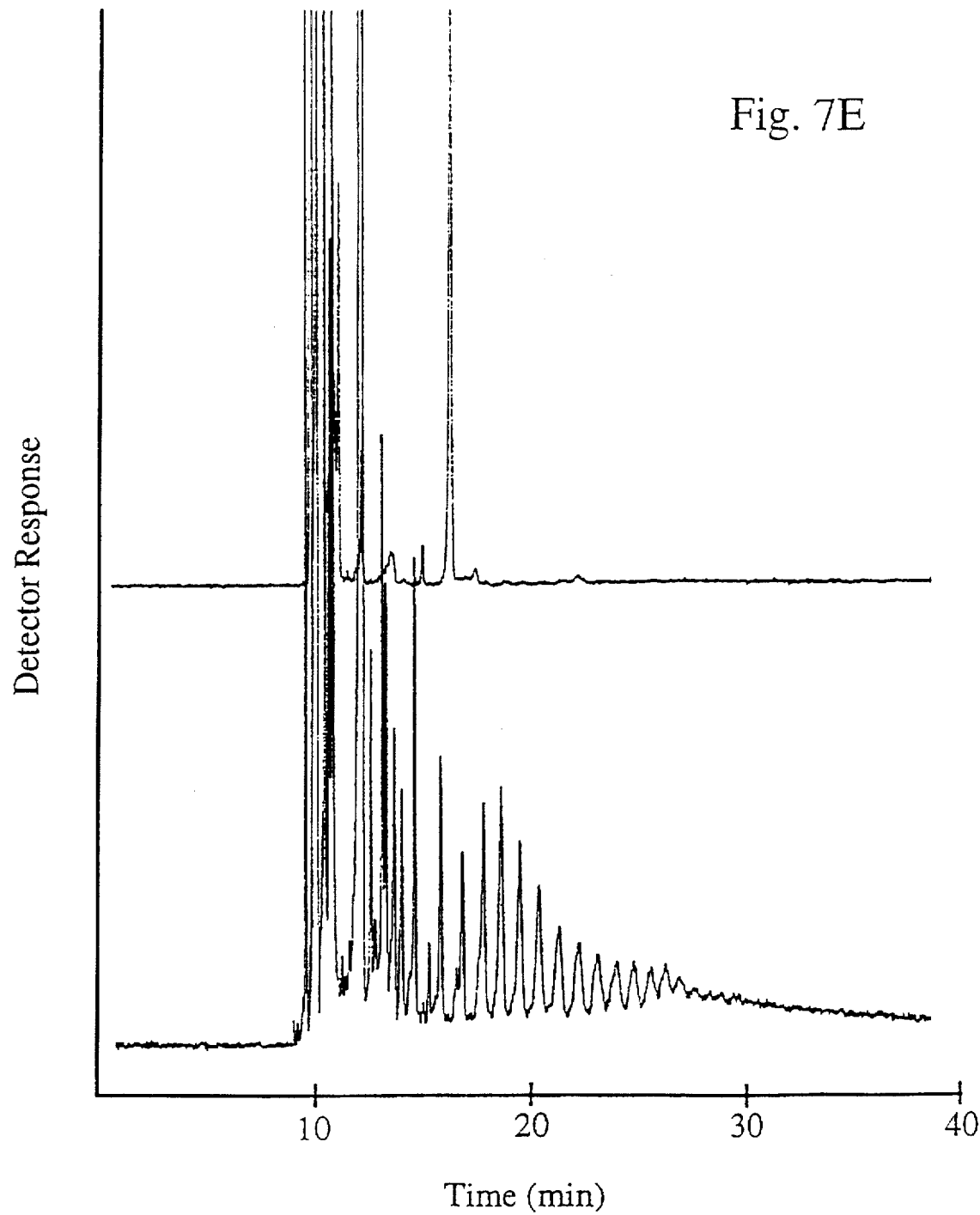
Figure 7F:
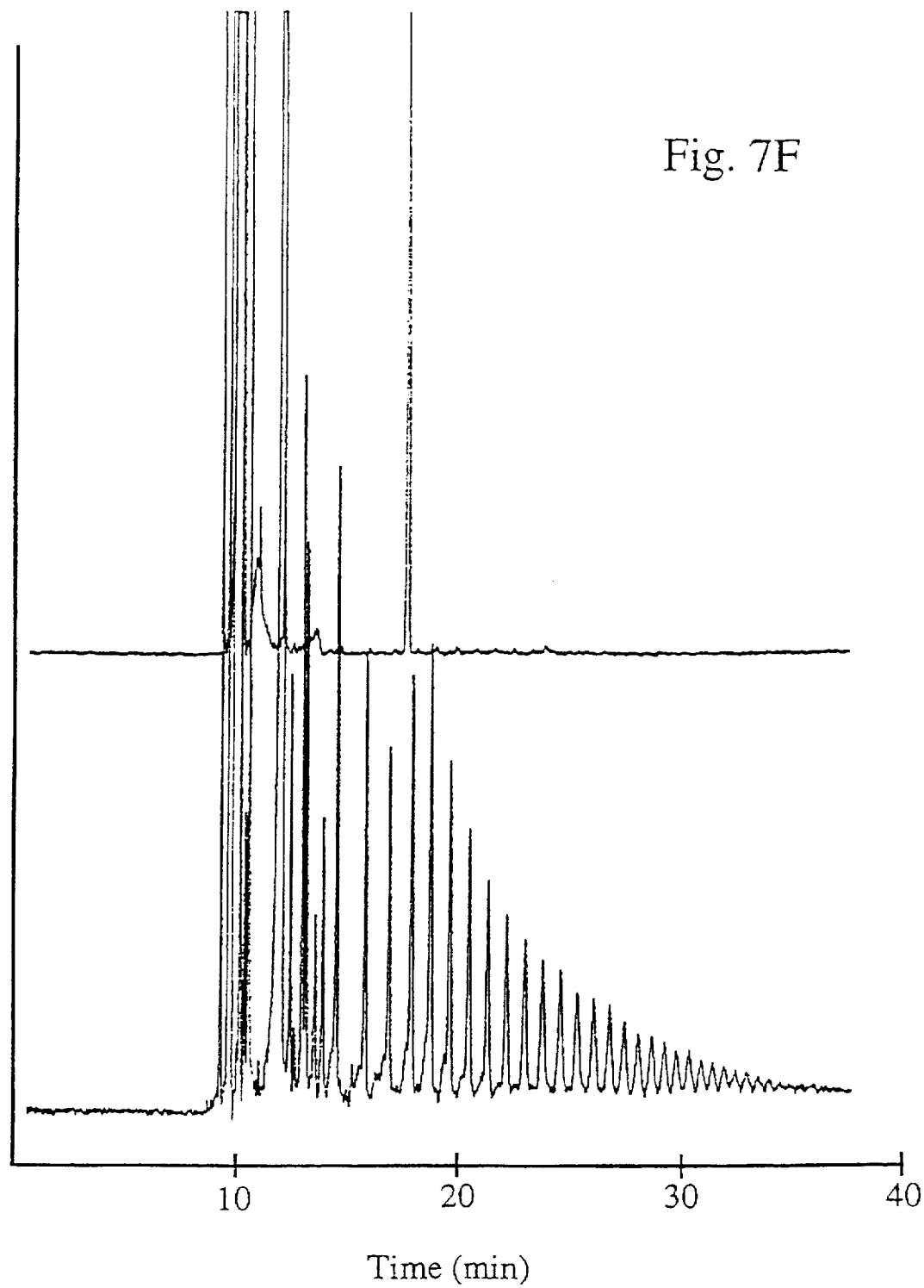
Figure 7G:
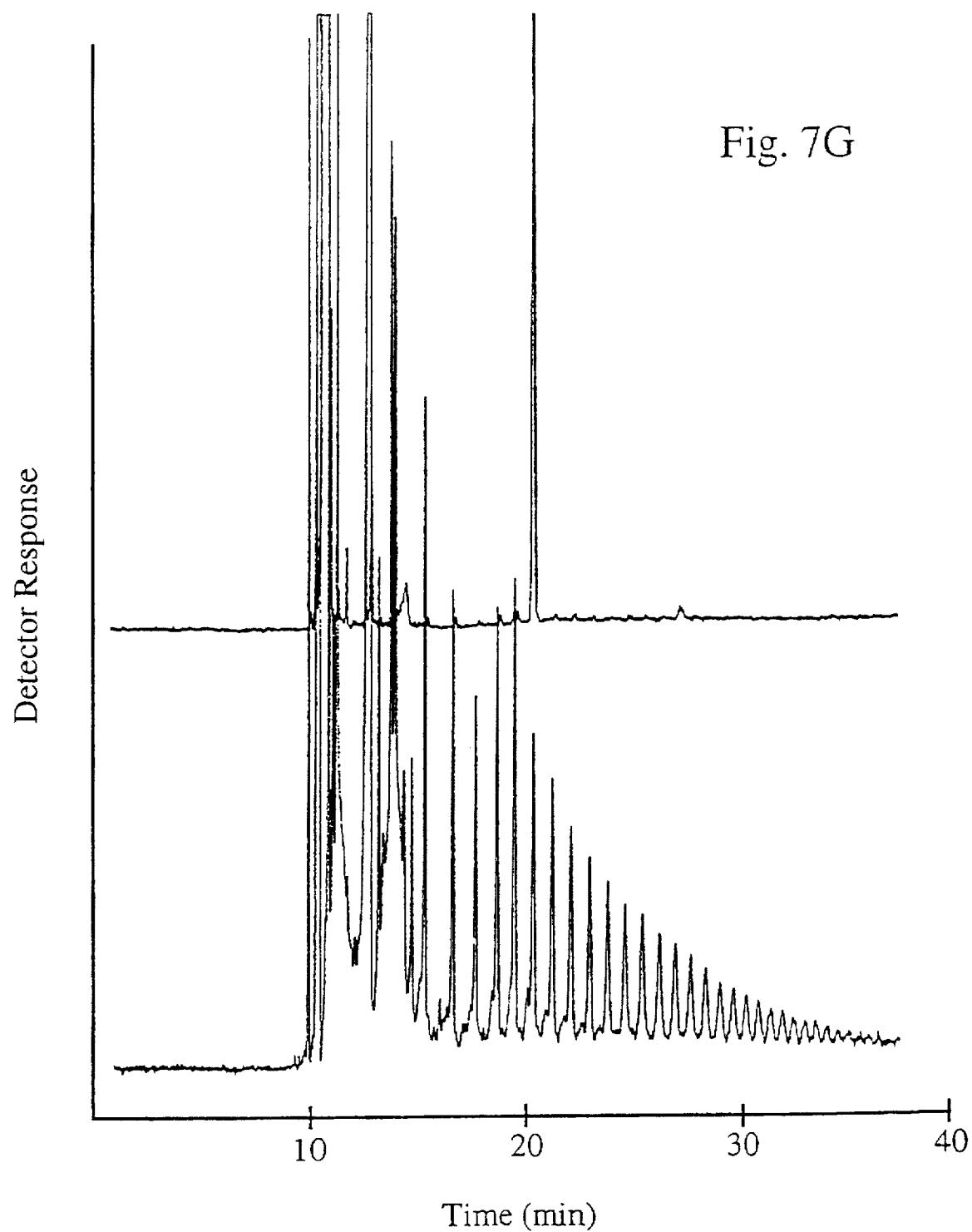

FIGS. 7A–7G show several representative examples of different combinations of carbohydrate sample, standard, and label. FIG. 7A shows a mixture of a M-150 internal standard labeled with 5-amino-2-naphthalenesulfonic acid and a maltohexaose sample labeled with 2-amino-1-naphthalenesulfonic acid, where in the top trace, EX=250 nm and EM=400 nm, and in the bottom trace, EX=250 nm and EM=520 nm. FIG. 7B shows a mixture of a M-150 internal standard labeled with 5-amino-2-naphthalenesulfonic acid and a maltopentaose sample labeled with 2-amino-1-naphthalenesulfonic acid, where in the top trace, EX=250 nm and EM=400 nm, and in the bottom trace, EX=250 nm and EM=520 nm. FIG. 7C shows a mixture of a M-150 internal standard labeled with 5-amino-2-naphthalenesulfonic acid and a maltotriaose sample labeled with 2-amino-1-naphthalenesulfonic acid, where in the top trace, EX=250 nm and EM=400 nm, and in the bottom trace, EX=250 nm and EM=520 nm. FIG. 7D shows a mixture of a M-150 internal standard labeled with 5-amino-2-naphthalenesulfonic acid and a maltopentaose sample labeled with 4-amino-1-naphthalenesulfonic acid, where in the top trace, EX=250 nm and EM=400 nm, and in the bottom trace, EX=250 nm and EM=520 nm. FIG. 7E shows a mixture of a M-040 internal standard labeled with 1-pyrenyloxyacethydrazide-3,6,8-trisulfonic acid and a maltotetraose sample labeled with 1-aminopyrene-3,6,8-trisulfonic acid, where in the top trace, EX=430 nm and EM=530 nm, and in the bottom trace, EX=376 nm and EM=436 nm. FIG. 7F shows a mixture of a M-040 internal standard labeled with 1-pyrenyloxyacethydrazide-3,6,8-trisultfonic acid and a maltopentaose sample labeled with 1-aminopyrene-3,6,8-trisulfonic acid, where in the top trace, EX=430 nm and EM=530 nm, and in the bottom trace, EX=376 nm and EM=436 nm. FIG. 7G shows a mixture of a M-040 internal standard labeled with 1-pyrenyloxyacethydrazide-3,6,8-trisulfonic acid and a maltoheptaose sample labeled with 1-aminopyrene-3,6,8-trisulfonic acid, where in the top trace, EX=430 nm and EM=530 nm, and in the bottom trace, EX=376 nm and EM=436 nm.

EXAMPLE 4

Introduction of Enzyme at the Transfer Cell

This example demonstrates an enzymatic reaction during a 2-D electrophoretic separation.

The apparatus configuration, buffers, electrophoresis operating conditions, capillary preparation, sample injection, first electrophoresis, and delay time measurement used in this example were the same as those used in Example 1.

Figure 8A:
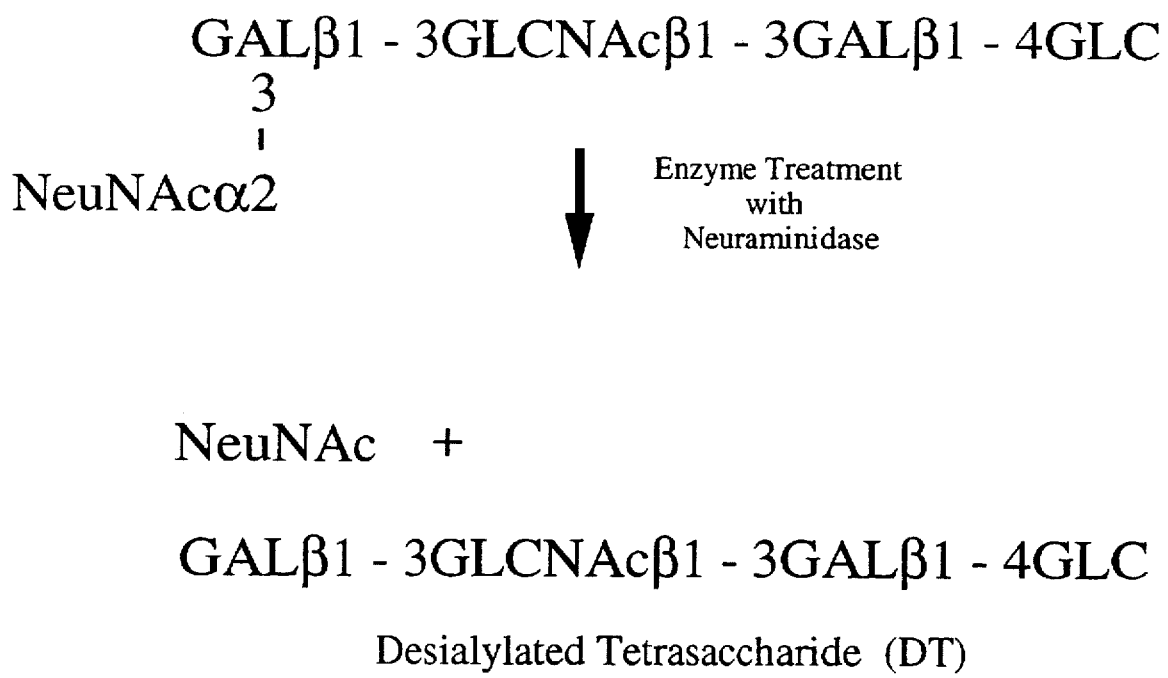
FIG. 8A–8D show the digestion of a sialylated pentasaccharide by the enzyme neuraminidase and the simultaneous addition of an internal standard using a transfer cell located between two CE capillaries.

The sample was a 0.05 mM solution of a sialylated pentasaccharide labeled with 4-aminonaphthalene-1-sulfonic acid. See FIG. 8A for the structure of sialylated pentasaccharide and the digestion products. The enzyme solution consisted of 25 U/ml neuraminidase in 50 mM sodium citrate buffer, pH 4.5. Combined with the enzyme was a 4-aminonaphthalene-1-sulfonic acid labeled M-150 maltodextrin internal standard.

Following the first electrophoresis, the first separation medium in the transfer cell was replaced by 100 μl of the enzyme-standard solution by removing the first transfer cell feed reservoir, replacing it with a second transfer cell feed reservoir containing the enzyme-standard solution, and pressurizing the second transfer cell feed reservoir at 5 psi for 2 s while all other vessels were vented to atmosphere. Next, to transfer the sialylated pentasaccharide peak across the gap in the transfer cell simultaneously with the transfer of an aliquot of enzyme-standard mixture, a hybrid electrokinetic-hydrodynamic transfer method was used 1.5 inches of mercury vacuum was applied to the second buffer reservoir while at the same time the first power supply was turned on for a period of one peak width, or approximately 5 s. The sample and enzyme were then allowed to incubate for ten minutes. After the enzyme incubation, the transfer cell feed reservoir was switched to one containing the second separation medium, the transfer cell was flushed with second separation medium, the second power supply was turned on, and the second electrophoresis was performed.

Figure 8B:
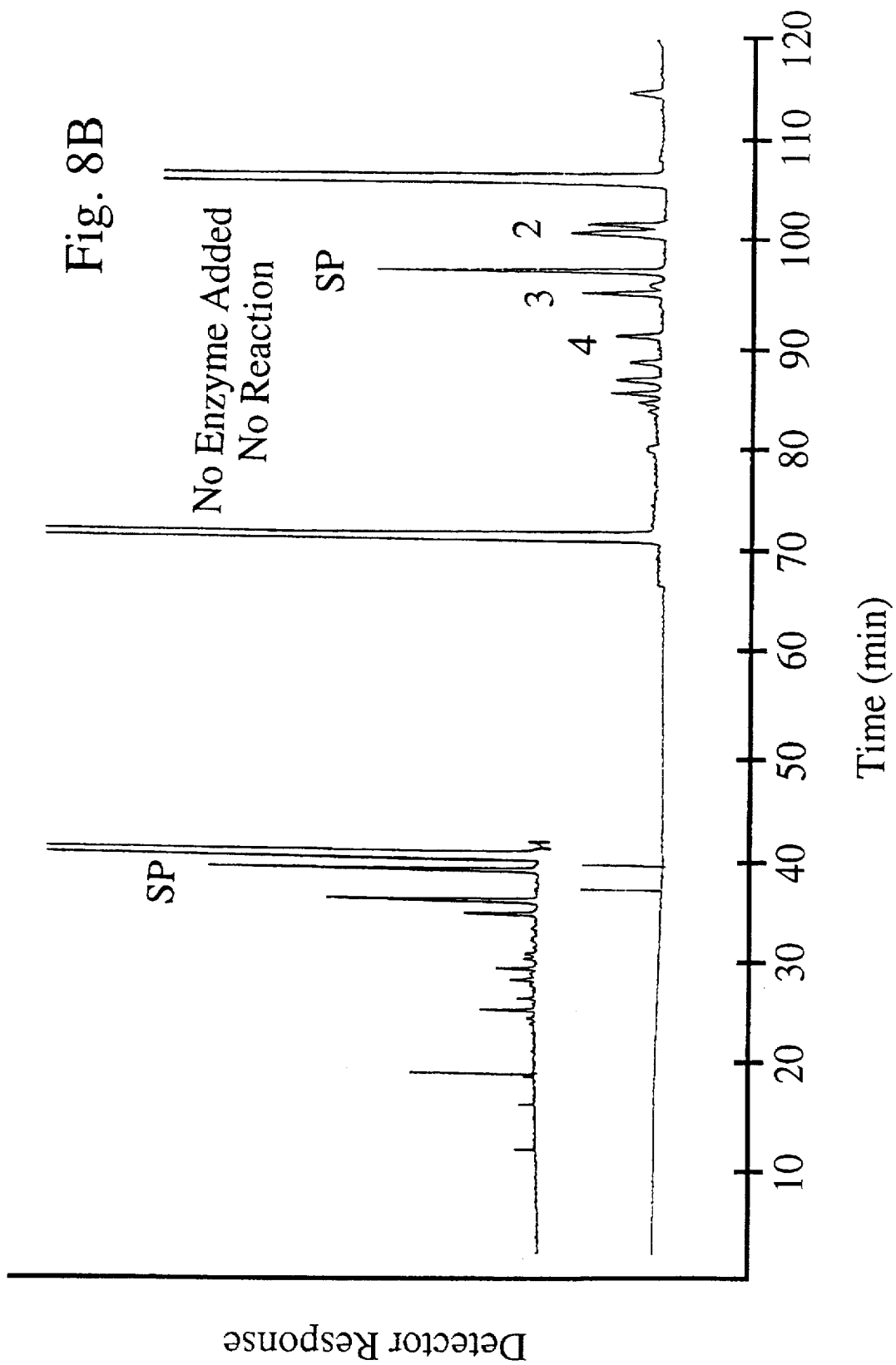
Figure 8C:
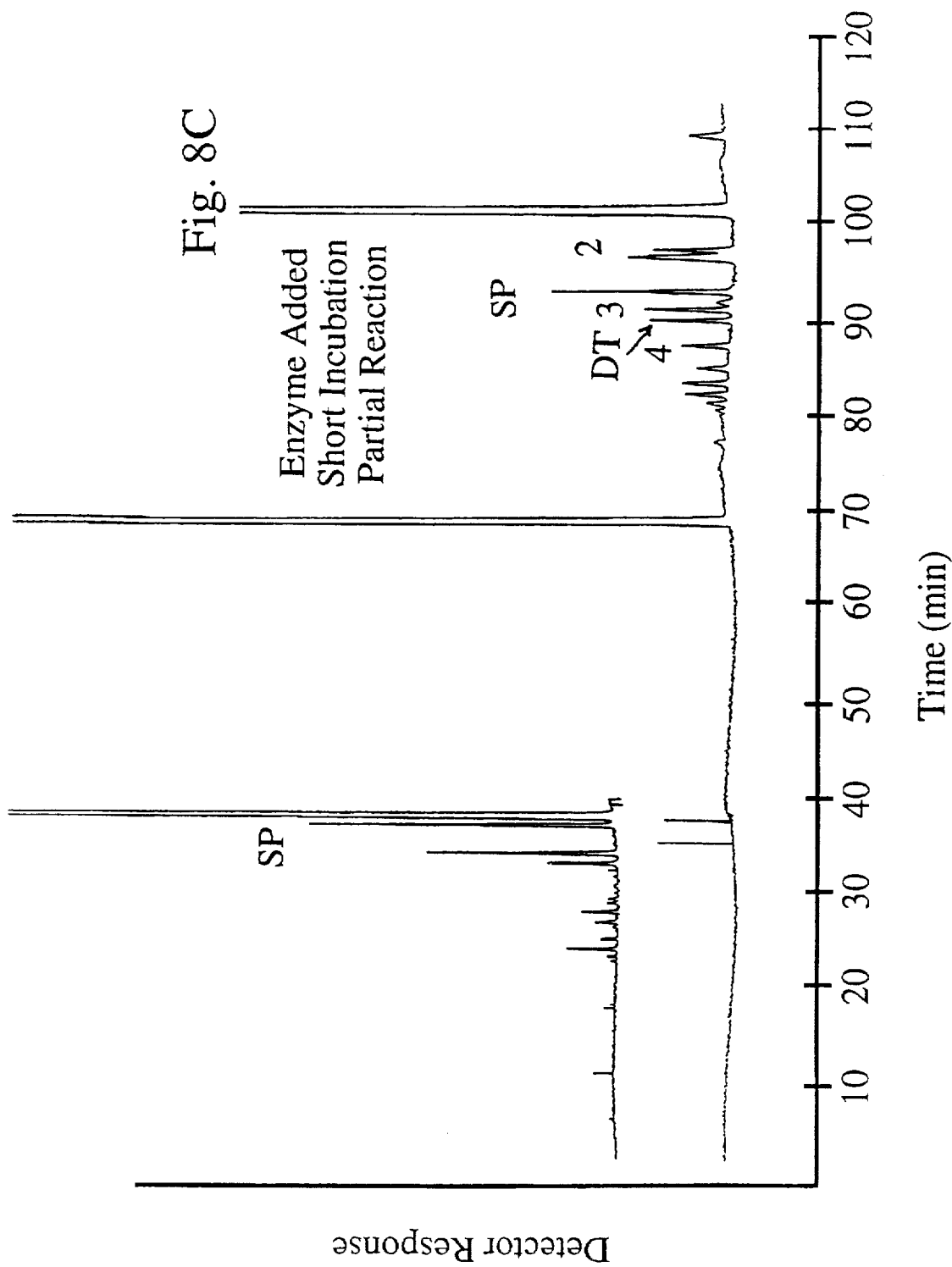
Figure 8D:
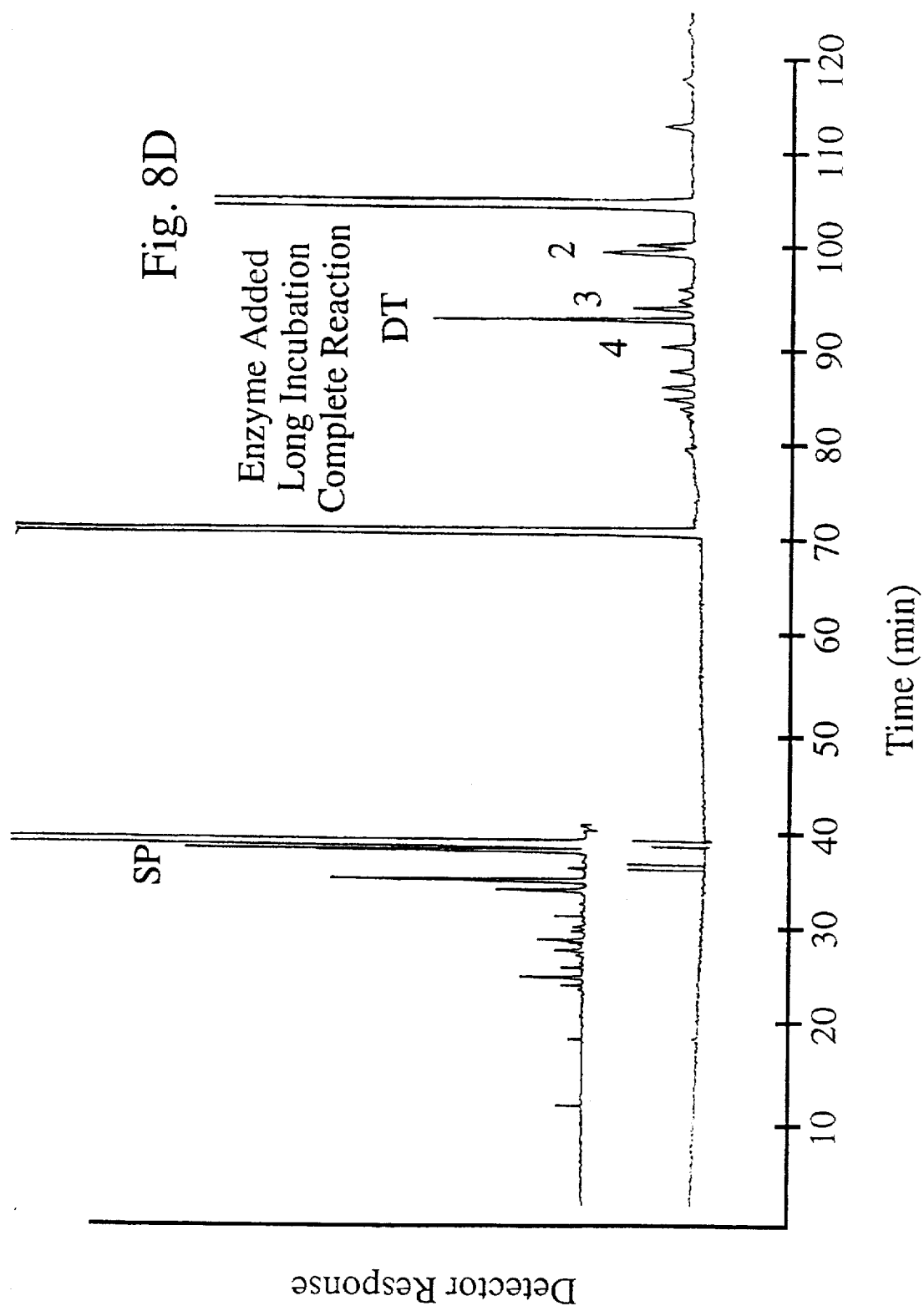

FIG. 8B shows the transfer of the sialylated pentasaccharide (SP) peak between the two separation capillaries with the introduction of the M-150 standard, where the numbers 2, 3, and 4 refer to the size of each ladder component in units of number of glucose units. Note that the sialylated pentasaccharide peak elutes between the 2- and 3-glucose-unit peaks. FIG. 8C shows the transfer of the sialylated pentasaccharide peak between the two separation capillaries with the introduction of the enzyme-maltodextrin standard mixture and a short incubation time resulting in the partial digestion of the sialylated pentasaccharide. Note the peak-height reduction seen for the sialylated pentasaccharide peak and the appearance of a new product peak, a desialylated tetrasaccharide (DT), between the 4- and 3-glucose-unit peaks. FIG. 8D shows the transfer of the sialylated pentasaccharide peak between the two separation capillaries with the introduction of the enzyme-maltodextrin standard and a long (10 min) incubation time resulting in complete digestion of the sialylated pentasaccharide.

Although the invention has been described with reference to various applications, methods, and compositions, it will be appreciated that various changes and modifications may be made without departing from the invention.

It is claimed:

1. An apparatus for performing electrophoresis of sample molecules comprising:

a first capillary for containing a first separation medium, having an inlet end, an outlet end, a bore, and a first detection region located proximate to the outlet end;

a second capillary, for containing a second separation medium, having an inlet end, an outlet end, a bore, and a second detection region located proximate to the outlet end;

an outlet transfer tube for directing material away from the outlet end of the first capillary and the inlet end of the second capillary, the outlet transfer tube having an inlet end, an outlet end, and a bore;

a transfer cell to which the outlet end of the first capillary, the inlet end of the second capillary, and the inlet end of the outlet transfer tube are connected so that there is communication among the bores of the first capillary, the second capillary, and the outlet transfer tube, such that the inlet end of the second capillary is disposed adjacent to the outlet end of the first capillary so that a gap is formed therebetween;

a high-voltage power supply means for providing an independently controllable electrical potential across the first capillary and the second capillary sufficient to cause electrophoresis of the sample;

a detection means for independently detecting the sample molecules at the first detection region and at the second detection region; and signal processing means for coordinating the high voltage power supply means and the detection means such that a selective transfer of a sample between the first and second capillaries can be effected.

2. The apparatus of claim 1 further including an inlet transfer tube for directing material to the outlet end of the first capillary and the inlet end of the second capillary, the inlet transfer tube having an inlet end, an outlet end, and a bore, the inlet end of the inlet transfer tube being connected to the transfer cell so that there is fluid communication among the bores of the inlet transfer tube, the first capillary, the second capillary, and the outlet transfer tube.

3. The apparatus of claim 2 wherein the ratio of the internal diameters of the outlet transfer tube and the inlet transfer tube is $\leq 2.0$, and the ratio of the internal diameters of the inlet transfer tube and the first capillary is $\leq 5.0$, and the ratio of the internal diameters of the inlet transfer tube and the second capillary is $\leq 5.0$.

4. The apparatus of claim 1 wherein the gap between the first capillary and the second capillary is approximately equal to d/2 where d is the internal diameter of one of these two capillaries.

5. The apparatus of claim 1 wherein the detection means is a uv absorbence detector.

6. The apparatus of claim 1 wherein the detection means is a fluorescence detector.

7. The apparatus of claim 6 wherein the fluorescence detector is capable of simultaneously detecting a plurality of fluorescence emission wavelengths.

8. A method for performing electrophoretic analysis of sample carbohydrate molecules comprising:

providing a first capillary, for containing a first separation medium, having an inlet end, an outlet end, and a first detection region located proximate to the outlet end;

providing a second capillary, for containing a second separation medium, having an inlet end, an outlet end, and a second detection region located proximate to the outlet end;

introducing the sample carbohydrate into the inlet end of the first capillary;

applying a voltage between the inlet end and the outlet end of the first capillary sufficient to cause electrophoresis of the sample towards the outlet end of the first capillary;

detecting a selected component of the sample at the first detection region, wherein the time of detection is $t_{detection}$;

computing a delay time for the selected component, $t_{delay}$;

turning off the voltage at time $t_{off}$ wherein $t_{off}=t_{detection}+t_{delay}$;

transferring the selected component across a transfer cell from the outlet end of the first capillary to the inlet end of the second capillary;

applying a voltage across the second capillary between the inlet end and the outlet end sufficient to cause electrophoresis of the selected component towards the outlet end of the second capillary; and detecting the selected sample component at the second detection region.

9. The method of claim 8 wherein a supplementary reagent is mixed with the selected component during the transfer step by flowing the supplementary reagent through the transfer cell using a transfer cell inlet tube and a transfer cell outlet tube during the transfer step.

10. The method of claim 9 wherein the supplementary reagent is an internal standard.

11. The method of claim 9 wherein the supplementary reagent is a probing reagent.

12. The method of claim 9 wherein the supplementary reagent is an enzyme.

13. A method for automated sequencing of mixtures of sample carbohydrate molecules comprising:

providing a first capillary, for containing a first separation medium, having an inlet end, an outlet end, and a first detection region located proximate to the outlet end;

providing a second capillary, for containing a second separation medium, having an inlet end, an outlet end, and a second detection region located proximate to the outlet end;

introducing the sample carbohydrate mixture into the inlet end of the first capillary;

applying a voltage between the inlet end and the outlet end of the first capillary sufficient to cause electrophoresis of the sample towards the outlet end of the first capillary;

detecting a selected component of the sample at the first detection region, wherein the time of detection is $t_{detection}$;

computing a delay time for the selected component, $t_{delay}$;

turning off the voltage at time $t_{off}$ wherein $t_{off}=t_{detection}+t_{delay}$;

transferring the selected component across a transfer cell from the outlet end of the first capillary to the inlet end of the second capillary, wherein during the transfer, the selected component is mixed with an enzyme reagent;

applying a voltage across the second capillary between the inlet end and the outlet end sufficient to cause electrophoresis of the selected component towards the outlet end of the second capillary;

detecting the selected sample component at the second detection region; correlating the electrophoretic migration behavior of the reaction products of the sample-enzyme reaction with the specificity of the enzyme reagent used; and repeating the above steps until the desired carbohydrate sequence is determined.

* * * * *